(12) United States Patent
Ginosar et al.

(10) Patent No.: US 7,592,282 B2
(45) Date of Patent: Sep. 22, 2009

(54) ENHANCEMENT OF ALKYLATION CATALYSTS FOR IMPROVED SUPERCRITICAL FLUID REGENERATION

(75) Inventors: Daniel M. Ginosar, Idaho Falls, ID (US); Lucia Petkovic, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 705 days.

(21) Appl. No.: 10/986,742

(22) Filed: Nov. 11, 2004

(65) Prior Publication Data

US 2006/0100089 A1    May 11, 2006

(51) Int. Cl.
*B01J 38/48* (2006.01)
*B01J 38/64* (2006.01)
*B01J 38/66* (2006.01)
*B01J 38/02* (2006.01)
*B01J 21/20* (2006.01)
*B01J 23/90* (2006.01)
*B01J 25/04* (2006.01)

(52) U.S. Cl. .................. 502/22; 502/20; 502/25; 502/26; 502/56

(58) Field of Classification Search .................. 502/214, 502/208, 22, 25, 26, 56
See application file for complete search history.

(56) References Cited

U.S. PATENT DOCUMENTS

| | | |
|---|---|---|
| 3,725,299 A | 4/1973 | Turnock et al. |
| 4,058,575 A | 11/1977 | Cahn et al. |
| 4,101,959 A | 7/1978 | Domike et al. |
| 4,124,528 A | 11/1978 | Modell |
| 4,568,786 A | 2/1986 | Hsia Chen et al. |
| 4,605,811 A | 8/1986 | Tiltscher et al. |
| 4,721,826 A | 1/1988 | Tiltscher et al. |
| 4,870,038 A | 9/1989 | Page et al. |
| 4,956,518 A | 9/1990 | Child et al. |

(Continued)

FOREIGN PATENT DOCUMENTS

CA    2273333    6/1998

OTHER PUBLICATIONS

Meier et al., "Atlas of Zeolite Structure Types," 2nd Rev Ed., Butterworths, 1987, pp. 1-152.

(Continued)

*Primary Examiner*—Karl E Group
*Assistant Examiner*—Noah S Wiese
(74) *Attorney, Agent, or Firm*—TraskBritt

(57) ABSTRACT

A method of modifying an alkylation catalyst to reduce the formation of condensed hydrocarbon species thereon. The method comprises providing an alkylation catalyst comprising a plurality of active sites. The plurality of active sites on the alkylation catalyst may include a plurality of weakly acidic active sites, intermediate acidity active sites, and strongly acidic active sites. A base is adsorbed to a portion of the plurality of active sites, such as the strongly acidic active sites, selectively poisoning the strongly acidic active sites. A method of modifying the alkylation catalyst by providing an alkylation catalyst comprising a pore size distribution that sterically constrains formation of the condensed hydrocarbon species on the alkylation catalyst or by synthesizing the alkylation catalyst to comprise a decreased number of strongly acidic active sites is also disclosed, as is a method of improving a regeneration efficiency of the alkylation catalyst.

13 Claims, 16 Drawing Sheets

U.S. PATENT DOCUMENTS

| | | | |
|---|---|---|---|
| 4,982,043 | A | 1/1991 | Hasselbring |
| 5,043,307 | A | 8/1991 | Bowes et al. |
| 5,177,298 | A | 1/1993 | Yon et al. |
| 5,237,120 | A | 8/1993 | Haag et al. |
| 5,250,484 | A * | 10/1993 | Beck et al. .................... 502/71 |
| 5,304,698 | A | 4/1994 | Husain |
| 5,310,713 | A | 5/1994 | Kojima et al. |
| 5,326,923 | A | 7/1994 | Cooper et al. |
| 5,345,028 | A | 9/1994 | Alerasool |
| 5,475,181 | A | 12/1995 | DiGuiseppi et al. |
| 5,489,732 | A | 2/1996 | Zhang et al. |
| 5,491,277 | A | 2/1996 | Stine et al. |
| 5,712,213 | A | 1/1998 | Joly et al. |
| 5,907,075 | A | 5/1999 | Subramaniam et al. |
| 5,916,835 | A | 6/1999 | Carroll et al. |
| 6,103,948 | A | 8/2000 | Ginosar et al. |
| 6,440,886 | B1 | 8/2002 | Gajda et al. |
| 6,579,821 | B1 * | 6/2003 | Ginosar et al. ................ 502/31 |
| 6,610,624 | B2 | 8/2003 | Horhota et al. |
| 6,613,708 | B1 * | 9/2003 | Ou et al. ........................ 502/64 |
| 2002/0160906 | A1 * | 10/2002 | Chen et al. .................... 502/63 |
| 2003/0008772 | A1 * | 1/2003 | Ma et al. ...................... 502/180 |
| 2003/0149321 | A1 * | 8/2003 | Mees et al. ................. 585/640 |
| 2003/0229246 | A1 * | 12/2003 | Leiber et al. ................. 562/17 |
| 2004/0063567 | A1 | 4/2004 | Ginosar et al. |

OTHER PUBLICATIONS

Chen et al., "Effects of surface modification on coking, deactivation and para-selectivity of H-ZSM-5 zeolites during ethylbenzene disproportionation," Journal of Molecular Catalysis A: Chemical 181 (2002) 41-55.

S.M. Csicsery, Catalysis by shape selective zeolites Science and technology, Pure & Appl. Chem. 58(6), 841(1986).

European Patent Office Supplementary European Search Report, Aug. 11, 2004.

Fan, L. et al., Supercritical-Phase Alkylation Reaction on Solid Acid Catalysts: Mechanistic Study and Catalyst Development, Ind. Eng. Chem. Res., vol. 36, 1997, pp. 1458-1463, XP002292033.

W. Hölderich, et al., Industrial application of zeolite catalysts in petrochemical processes, Ger. Chem. Eng. 8, 337 (1985).

W. Hölderich, et al., Zeolites: Catalysts for organic syntheses, Angew. Chem. Int. Ed. Engl. 27, 226 (1988).

Inui et al., "Effect of Modification of Acid Sites Located on the External Surface of a Gallium-Silicate Crystalline Catalyst on Reducing Coke Deposit in Paraffin Aromatization," Ind. Eng. Chem. Res. 1997, 36, 4827-4831.

Kirk Othmer Encyclopedia of Chemical Technology, vol. 21, pp. 770 800, 3rd ed. (1983).

Liu et al., "Surface modification of zeolite Y and mechanism for reducing naphtha olefin formation in catalytic cracking reaction," Applied Catalysis A: General 264 (2004) 225-228.

J.A. Martens, et al., Estimation of the void structure and pore dimensions of molecular sieve zeolites using the hydroconversion of n decane, Zeolites 4, 98 (1984).

Petkovic et al., "The effect of supercritical isobutane regeneration on the nature of hydrocarbons deposited on a USY zeolite catalyst utilized for isobutane/butane alkylation," Applied Catalysis A: General xxx (2004) xxx-xxx.

Petkovic et al., "Characterization of Coke Deposited on USY Zeolite Catalyst Under Isobutane/butane Alkylation Reaction and Supercritical Isobutane Regeneration," 18$^{th}$ Annual Symposium of the Western States Catalysis Club, Feb. 27, 2004, 25 pages.

Seapan, M. et al., Chapter 9 Decoking and Regeneration of a Hydrotreating Catalyst by Supercritical Extraction, 1989, American Chemical Society.

West, Phillip B., et al., "Clamping systems for Large Downhole Seismic Sensor Arrays," Idaho National Engineering and Environmental Laboratory, Jun. 2001.

Zhao, Dongbin et al., "Ionic Liquids: Applications in Catalysis," Catalysis Today 74 (2002) 157-189.

Zurer, P., Green Organic Synthesis Dives into Near-Critical Water, C&EN, Jan. 3, 2000, pp. 26-27.

Hammershaimb, H.U. et al., "Alkylation," Encyclopedia of chemical Technology, 4th Edition, vol. 2, 1992, pp. 85-112.

"Material Safety Data Sheet, Benzene MSDS," Science Lab.com, accessed Jan. 19, 2008, pp. 1-8.

"Material Safety Data Sheet, Isobutylene," Airgas, accessed Jan. 19, 2008, pp. 1-5.

International Search Report for International Application No. PCT/US05/40546.

Written Opinion of the International Searching Authority from PCT/US05/40546, dated Jun. 3, 2008, 7 pages.

* cited by examiner

ENHANCEMENT OF ALKYLATION CATALYSTS FOR IMPROVED SUPERCRITICAL FLUID REGENERATION

GOVERNMENT RIGHTS

The United States Government has rights in the following invention pursuant to Contract No. DE-AC07-99ID13727 between the U.S. Department of Energy and Bechtel BWXT Idaho, LLC.

FIELD OF THE INVENTION

The present invention relates to a method of modifying a surface of a catalyst. More specifically, the present invention relates to a method of modifying an alkylation catalyst to reduce formation of condensed hydrocarbon species on the alkylation catalyst.

BACKGROUND OF THE INVENTION

Alkylation reactions are used to add an alkyl group to a molecule that is to be alkylated. Alkylation reactions are extensively used in the petroleum industry to produce medium- or large-mass hydrocarbons from smaller molecules. The alkylation reaction is typically used to alkylate a high vapor pressure paraffin (an alkane) with an olefin (an alkene) to produce a low vapor pressure, high-octane gasoline blend. This gasoline blend is a clean gasoline blend stream and provides 13%-15% of gasoline demand in the United States. One important alkylation reaction in the petroleum industry is the alkylation of isobutane with butene to produce isooctane. Currently, the alkylation reaction is catalyzed with a concentrated liquid mineral acid, such as hydrofluoric acid or sulfuric acid. However, large acid volumes and acid-oil sludges are produced by the mineral acid-catalyzed reaction, raising safety and environmental concerns. Disposal of the acid-oil sludge is subject to stringent environmental regulations, which adds considerable expense to the alkylation reaction. In addition, leakage of the acid, either as a liquid or a solid, is another significant safety concern.

To reduce the environmental concerns, solid alkylation catalysts have been used to catalyze the reaction. However, these solid alkylation catalysts deactivate rapidly due to the accumulation of hydrocarbon species (also known as coke) on a surface of the solid alkylation catalyst. Coking of the solid alkylation catalyst is caused by side reactions that involve acid-catalyzed polymerization and cyclization of the reactants and/or reaction products, which produces high molecular-weight compounds that undergo extensive dehydrogenation, aromatization, and further condensation. As the hydrocarbon species accumulate, they deactivate the solid alkylation catalyst and decrease its ability to effectively catalyze the alkylation reaction. These hydrocarbon species are difficult to remove from the solid alkylation catalyst. The solid alkylation catalyst is typically regenerated or reactivated by burning off or gasifying the coke compounds. However, since these regeneration processes are oxidative and damage activity of the solid alkylation catalyst, the solid alkylation catalyst is only capable of being regenerated a few times. The rapid deactivation of the solid acid catalyst also produces large volumes of the solid alkylation catalyst that must be discarded, making the alkylation reaction and subsequent regeneration of the solid alkylation catalyst economically and environmentally unacceptable.

U.S. Pat. No. 6,579,821 to Ginosar et al. (the "Ginosar '821 patent"), the disclosure of which is incorporated by reference herein, discloses the use of a supercritical fluid to regenerate the alkylation catalyst. The supercritical fluid is isobutane, isopentane, 2,3-dimethylbutane, 2-methylpentane, 3-methylpentane, 2,3-dimethylpentane, 2,4-dimethylpentane, 2-methylhexane, 3-methylhexane, 2,3-dimethylhexane, 2,4-dimethylhexane, 2,5-dimethylhexane, 3,4-dimethylhexane, or 2,3,4-trimethylhexane. Extractive properties of the supercritical fluid are used to remove the hydrocarbon species that are adsorbed onto the alkylation catalyst. As the supercritical fluid contacts the alkylation catalyst, the adsorbed hydrocarbon species are dissolved and removed. The supercritical fluid regeneration process enables the alkylation catalyst to be reactivated or regenerated more than fifty times.

While the supercritical fluid removes most of the hydrocarbon species, the supercritical fluid has limited ability to effectively remove condensed hydrocarbon species that are present on the alkylation catalyst. As used herein, the term "condensed hydrocarbon species" refers to a hydrocarbon compound(s) that is formed by an alkylation or oligomerization reaction, followed by cyclization and/or dehydrogenation of the hydrocarbon species. As the condensed hydrocarbon species accumulate on the alkylation catalyst, they limit the extent of regeneration and the economics of using the supercritical fluid regeneration process.

Surface modification of catalysts used in various types of reactions is known in the art to increase performance (activity) or to decrease deactivation of the catalyst. As disclosed in Liu et al., "Surface modification of zeolite Y and mechanism for reducing naphtha olefin formation in catalytic cracking reaction," App. Catal. A: General, 264:225-228 (2004), a surface of zeolite Y is modified with a rare earth compound and a phosphorus compound to improve acidity density and strength in pores of the zeolite Y and to decrease surface acidity density of the zeolite Y. As disclosed in Inui et al., "Effect of Modification of Acid Sites Located on the External Surface of a Gallium-Silicate Crystalline Catalyst on Reducing Coke Deposit in Paraffin Aromatization," Ind. Eng. Chem. Res., 36:4827-4831 (1997), acid sites on an external surface of MFI-type gallium-silicate crystals are selectively modified with cerium oxide. The cerium oxide is used to neutralize the acid sites, moderating deactivation of the MFI-type gallium-silicate crystals and reducing deposition of coke compounds on the MFI-type gallium-silicate crystals. Chen et al., "Effects of surface modification on coking, deactivation and para-selectivity of H-ZSM-5 zeolites during ethylbenzene disproportionation," J. Molec. Catal. A: Chemical, 181: 41-55 (2002), discloses modifying a surface of an H-ZSM-5 zeolite by silica chemical vapor deposition ("Si-CVD") or by a combination of lepidine adsorption and Si-CVD to improve the performance of the H-ZSM-5 zeolite.

U.S. Pat. No. 6,440,886 to Gajda et al. discloses a surface-modified beta zeolite that has decreased deactivation. The beta zeolite is used to catalyze alkylation or transalkylation of an aromatic compound. The surface of the beta zeolite is modified by removing strong acid sites, such as by converting the strong acid sites to weaker acid sites that are ineffective or less effective. To modify the catalyst, the beta zeolite is exposed to a strong mineral acid, such as nitric acid, sulfuric acid, phosphoric acid, or hydrochloric acid. The beta zeolite is then calcined at a temperature ranging from 550° C. to 700° C. In U.S. Pat. No. 5,043,307 to Bowes et al., a modified aluminosilicate zeolite is disclosed. The aluminosilicate zeolite is modified by steaming to decompose template material and to remove zeolitic aluminum. The zeolite is then contacted with a dealuminizing agent to form a water-soluble aluminum complex. U.S. Pat. No. 5,237,120 to Haag et al. discloses isomerizing a terminal double bond olefin-containing organic feedstock to an internal double bond olefin. The isomerization reaction is performed using a surface-modified double bond isomerization catalyst that is partially deactivated for acid catalyzed reactions. The double bond isomerization catalyst is modified by chemisorbing a surface-deactivating agent to the surface. The surface-deactivating agent is an amine, phosphine, phenol, polynuclear hydrocarbon, cationic dye, or organic silicon compound.

BRIEF SUMMARY OF THE INVENTION

The present invention relates to a method of modifying an alkylation catalyst to reduce the formation of condensed hydrocarbon species on a surface thereof. The method comprises providing an alkylation catalyst comprising a plurality of active sites. The alkylation catalyst may be selected from the group consisting of a zeolite, silicate, aluminophosphate, sodium calcium silicoaluminate, silicoaluminophosphate, pillared silicate, clay, layered material, sulfated zirconia, alumina, silica, boria, phosphorous oxide, titanium dioxide, zirconium dioxide, chromia, zinc oxide, magnesia, calcium oxide, silica-alumina, silica-magnesia, silica-alumina-magnesia, silica-alumina-zirconia, sulfated mixed-metal oxide, bauxite, diatomaceous earth, and mixtures thereof. The plurality of active sites on the alkylation catalyst may include a plurality of weakly acidic active sites, intermediate acidity active sites, and strongly acidic active sites. A base is adsorbed to a portion of the plurality of active sites to selectively poison the portion of the plurality of active sites, wherein the base prevents the formation of condensed hydrocarbon species on the portion of the plurality of active sites. In one embodiment, the base may selectively poison the strongly acidic active sites. The base may be selected from the group consisting of ammonia, an amine, phosphine, pyridine, a substituted pyridine, acetonitrile, benzene, a benzene derivative, and mixtures thereof.

The present invention also relates to a method of modifying an alkylation catalyst to reduce the formation of condensed hydrocarbon species thereon by at least one of providing an alkylation catalyst comprising a pore size distribution that sterically constrains formation of a condensed hydrocarbon species on the alkylation catalyst and synthesizing the alkylation catalyst to comprise a decreased number of strongly acidic active sites. The pore size distribution on the alkylation catalyst may be selected so that the pore size distribution is smaller than a size of the condensed hydrocarbon species. In one embodiment, the pore size distribution may range from approximately 5 Å to approximately 8 Å. The alkylation catalyst may comprise a decreased number of strongly acidic active sites by synthesizing a zeolite comprising a silicon/aluminum ("Si/Al") ratio ranging from approximately 2.5 to approximately 15.

The present invention also relates to a method of improving a regeneration efficiency of an alkylation catalyst. The method comprises providing an alkylation catalyst comprising a plurality of active sites. The active sites may comprise a plurality of weakly acidic active sites, intermediate acidity active sites, and strongly acidic active sites. A base is adsorbed to a portion of the plurality of active sites and may be selected from the group consisting of ammonia, an amine, phosphine, pyridine, a substituted pyridine, acetonitrile, benzene, a benzene derivative, and mixtures thereof. The base may be adsorbed to the strongly acidic active sites. The base prevents the formation of condensed hydrocarbon species on the alkylation catalyst. The alkylation catalyst is used to catalyze an alkylation reaction. During the alkylation reaction, hydrocarbon species may form on the alkylation catalyst. The alkylation catalyst is exposed to supercritical fluid regeneration to substantially regenerate the alkylation catalyst by substantially removing the hydrocarbon species from the alkylation catalyst.

The present invention also relates to a method of improving a regeneration efficiency of an alkylation catalyst. The method comprises providing an alkylation catalyst comprising a pore size distribution that sterically constrains formation of condensed hydrocarbon species on the alkylation catalyst. The pore size distribution may be selected to be smaller than a size of the condensed hydrocarbon species. In one embodiment, the pore size distribution ranges from approximately 5 Å to approximately 8 Å. The alkylation catalyst is used to catalyze an alkylation reaction, in which hydrocarbon species may be formed on the alkylation catalyst. The alkylation catalyst is exposed to supercritical fluid regeneration to substantially regenerate the alkylation catalyst by substantially removing the hydrocarbon species.

The present invention also relates to a method of improving a regeneration efficiency of an alkylation catalyst that comprises synthesizing the alkylation catalyst to comprise a decreased number of strongly acidic active sites. The decreased number of strongly acidic active sites prevents the formation of condensed hydrocarbon species on the alkylation catalyst. In one embodiment, the alkylation catalyst may be a zeolite comprising a silicon/aluminum ratio ranging from approximately 2.5 to approximately 15. The alkylation catalyst is used to catalyze an alkylation reaction, in which hydrocarbon species may be formed on the alkylation catalyst. The alkylation catalyst is exposed to supercritical fluid regeneration to regenerate the alkylation catalyst by substantially removing the hydrocarbon species.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
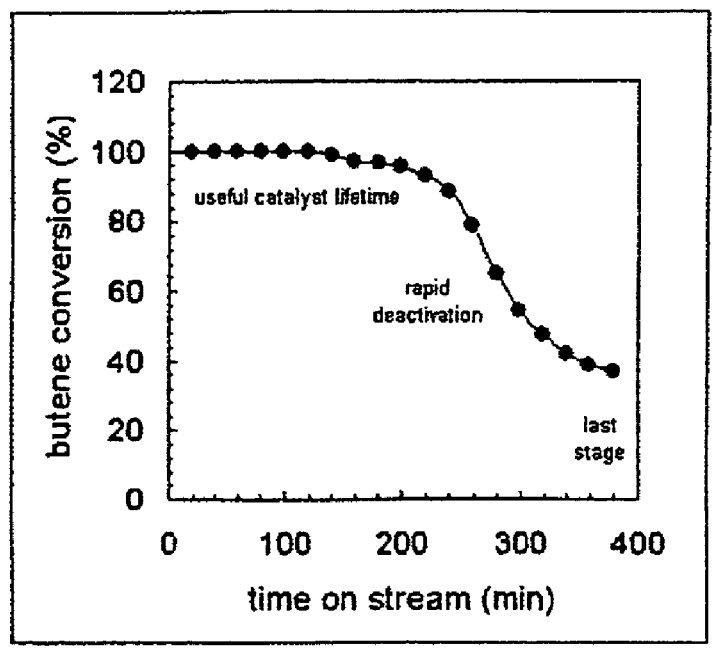
FIG. 1 shows a plot of USY zeolite activity as measured by butene conversion.

An alkylation catalyst having a modified surface is disclosed. The modified surface substantially reduces or eliminates formation of condensed hydrocarbon species on the alkylation catalyst. When present, the condensed hydrocarbon species reduce the effectiveness of supercritical fluid regeneration of the alkylation catalyst. The surface of the alkylation catalyst may be modified by at least one of selectively poisoning a portion of active sites on the alkylation catalyst, by selecting a pore size distribution on the alkylation catalyst to hinder formation of the condensed hydrocarbon species, and by manufacturing the alkylation catalyst to include fewer sites that are active for the formation of the condensed hydrocarbon species. By reducing the formation of the condensed hydrocarbon species, the alkylation catalyst may be more effectively regenerated or reactivated by the supercritical fluid regeneration. The supercritical fluid regeneration may also be performed at less frequent intervals, allowing the alkylation catalyst to be used for a longer period of time before regeneration is needed. The alkylation catalyst having the modified surface may also be regenerated in a shorter amount of time and may have an increased longevity than an alkylation catalyst lacking the surface modification.

As described in more detail herein, the condensed hydrocarbon species may be polyolefinic hydrocarbons, aromatic hydrocarbons, dehydrogenated aromatic hydrocarbons, cyclic or polycyclic hydrocarbons, graphitic coke compounds, or mixtures thereof. These condensed hydrocarbon species may be formed during an alkylation reaction catalyzed by the alkylation catalyst or during regeneration or reactivation of the alkylation catalyst. As used herein, the terms "regenerate," "reactivate," or other verb forms thereof refer to treating the alkylation catalyst to render the alkylation catalyst into a form in which it is suitable for efficient use or reuse as the alkylation catalyst. The condensed hydrocarbon species may have greater than or equal to 9 carbon atoms and may arise primarily from oligomerization, dehydrogenation, or cyclization of reactants or products of the alkylation reaction. Precursors or reaction intermediates for the condensed hydrocarbon species may include, but are not limited to, allylic carbocations, monoenylic carbocations, dienylic carbocations, polyenylic carbocations, or mixtures thereof.

The alkylation catalyst may be modified to reduce a number of sites on its surface that are active for the formation of the condensed hydrocarbon species. As such, the formation of the condensed hydrocarbon species on the alkylation catalyst may be reduced or eliminated. The number of active sites may be decreased to a number sufficient to prevent the formation of the condensed hydrocarbon species without substantially affecting the catalytic performance of the alkylation catalyst. In other words, a sufficient number of total active sites may remain on the alkylation catalyst to catalyze the alkylation reaction. However, the number of active sites that may contribute to the formation of the condensed hydrocarbon species may be substantially reduced.

The alkylation catalyst may be a solid alkylation catalyst having sufficient strength to catalyze the alkylation reaction. The alkylation catalyst may include a plurality of acidic active sites, which are present in a distribution of acidities that ranges from weakly acidic to strongly acidic. In other words, the acidic active sites may include weakly acidic active sites, active sites that are intermediate in acidity, and strongly acidic active sites. Out of these acidic active sites, the weakly acidic active sites and the intermediate acidity active sites may not substantially contribute to the formation of the condensed hydrocarbon species. However, it is believed that the most acidic, or strongly acidic, active sites may be substantially responsible for the formation of the condensed hydrocarbon species. Therefore, to prevent the condensed hydrocarbon species from forming, the number of strongly acidic active sites on the alkylation catalyst may be reduced. For instance, the number of strongly acidic active sites may be decreased by from approximately 10% to approximately 20% compared to the number of strongly acidic active sites on a conventional solid alkylation catalyst that lacks the surface modifications. To maintain the performance of the alkylation catalyst, the corresponding activity of the alkylation catalyst may decrease less than approximately 10%. Alternatively, the strongly acidic active sites may be selectively poisoned so that the condensed hydrocarbon species are unable to form on the alkylation catalyst.

To quantify or describe the relative acidities (weakly acidic, intermediate acidity, or strongly acidic) of the active sites, an amount of ammonia that adsorbs to the surface of the alkylation catalyst at different temperatures may be used. The total number of acidic active sites (weakly acidic active sites, intermediate acidity active sites, and strongly acidic active sites) may be determined by the amount of ammonia adsorbed to the alkylation catalyst at 175° C. The ammonia may desorb from a portion of the acidic active sites by evacuation at a temperature of 175° C. The active sites from which the ammonia desorbs at a temperature of 175° C. are referred to herein as the "weakly acidic active sites." In other words, the weakly acidic active sites are not able to retain adsorbed ammonia under evacuation at 175° C. while the intermediate acidity active sites and the strongly acidic active sites retain adsorbed ammonia at this temperature. The amount of ammonia that remains adsorbed to the alkylation catalyst (i.e., the amount of ammonia that does not desorb from the alkylation catalyst) may be used to determine the number of intermediate acidity active sites and strongly acidic active sites. The acidities of the remaining active sites may be determined using a temperature gradient that ranges from approximately 175° C. to approximately 540° C. At increasing temperatures, the ammonia may desorb from the remaining acidic active sites, giving a profile from which the number of intermediate acidity active sites and strongly acidic active sites may be determined. The acidic active sites on which the ammonia remains adsorbed at a temperature greater than or equal to approximately 450° C. are referred to herein as the "strongly acidic active sites," while the acidic sites from which the ammonia desorbs at a temperature ranging from approximately 175° C. to approximately 450° C. are referred to as the "intermediate acidity active sites." In general, the total number of acidic active sites on the alkylation catalyst may correspond to greater than 0.7 millimole of ammonia adsorbed per gram of alkylation catalyst, the intermediate acidity active site may correspond to greater than approximately 0.2 millimole of ammonia adsorbed per gram of alkylation catalyst, and the strongly acidic active sites may correspond to less than approximately 0.05 millimole of ammonia adsorbed per gram of alkylation catalyst.

The alkylation catalyst may be selected by one of ordinary skill in the art depending on the alkylation reaction to be catalyzed. The alkylation catalyst may be a solid alkylation catalyst that has the acidic active sites or is capable of achieving the acidic active sites when properly treated, as known in the art. The alkylation catalyst may include, but is not limited to, a molecular sieve, such as a zeolite, silicate, aluminophosphate ("ALPO"), silicoaluminate, silicoaluminophosphate ("SAPO"), other metal aluminophosphates, a pillared silicate, clay (including kaolin and bentonite), a layered material, or mixtures thereof. The zeolite may be a natural zeolite, a synthetic zeolite, or mixtures thereof. The zeolite may include, but is not limited to, a zeolite having the framework structure of FAU, MFI, MAZ, EMT, MEI, MTW, FER, EUO, MWW, OFF, MOR, BEA, LTL, zeolites that include rare-earth metals, or mixtures thereof. In referring to the zeolites, standard nomenclature (as published by the International Zeolite Association) has been used. Specific commercial examples of the zeolites include, but are not limited to, Zeolite Socony Mobil-4 ("ZSM-4"), ZSM-3, ZSM-5, ZSM-20, ZSM-18, ZSM-12, ZSM-35, ZSM-48, ZSM-50, Mobil Composition of Matter-22 ("MCM-22"), PSH-3, TMA offretite, TEA mordenite, REY ("Rare Earth Y zeolite"), faujasites including zeolite Y, mordenite, ultrastable Y zeolites ("USY"), zeolite beta, zeolite omega, zeolite L, clinoptilolite, zeolites that include rare-earth metals, or mixtures thereof. Zeolites are commercially available from numerous manufacturers, such as Mallinckrodt Baker Inc. (Phillipsburg, N.J.), or Zeolyst International (Valley Forge, Pa.). Examples of the aluminophosphate include, but are not limited to, ALPO-5, Virginia Polytechnic Institute-5 ("VPI-5"), or mixtures thereof. Examples of silicoaluminophosphates include, but are not limited to, SAPO-5, SAPO-37, SAPO-31, SAPO-40, SAPO-41, or mixtures thereof. An example of the layered material includes MCM-36.

The alkylation catalyst may also be a sulfated zirconia ("S/$ZrO_2$") catalyst, which is prepared by exposing zirconium hydroxide to sulfuric acid. The alkylation catalyst may also be an inorganic oxide, such as alumina (including beta- or gamma-alumina), silica, boria, a phosphorous oxide, titanium dioxide, zirconium dioxide, chromia, zinc oxide, magnesia, calcium oxide, silica-alumina, silica-magnesia, silica-alumina-magnesia, silica-alumina-zirconia, a sulfated mixed-metal oxide, bauxite, diatomaceous earth, or mixtures thereof.

The alkylation catalyst may be used in combination with a non-zeolite substance, such as a Lewis acid. The Lewis acid may be boron trifluoride, antimony pentafluoride, aluminum trichloride, or mixtures thereof. A refractory oxide may also be used in combination with the alkylation catalyst to provide temperature resistance. In addition, a diluent material, such as an oxide or clay, may be used with the alkylation catalyst to control the conversion rate, to improve mechanical properties of the alkylation catalyst, to provide a matrix material, or to act as a binder. Other active substances, such as platinum, palladium, or mixtures thereof, may also be used with the alkylation catalyst to provide a metal hydrogenation function.

In one embodiment, the number of active sites on the alkylation catalyst may be decreased by selectively poisoning at least a portion of the acidic active sites on the alkylation catalyst. Since the strongly acidic active sites, as defined above, are believed to be responsible for the formation of the condensed hydrocarbon species, the portion of the acidic active sites that are selectively poisoned may be the strongly acidic active sites. By selectively poisoning the strongly acidic active sites, the condensed hydrocarbon species may be prevented from forming on the alkylation catalyst. The strongly acidic active sites may be selectively poisoned by exposing the alkylation catalyst to a base, such as ammonia, an amine, phosphine, pyridine, a substituted pyridine, acetonitrile, benzene, a benzene derivative, or mixtures thereof. The alkylation catalyst may be exposed to the base at a sufficient temperature and for a sufficient amount of time to adsorb the base to the active sites, such as at a temperature ranging from approximately 100° C. to approximately 500° C. The base may also be adsorbed to the active sites under vacuum conditions by placing the alkylation catalyst in a chamber and evacuating the chamber. The base may be allowed to enter into the evacuated chamber and adsorb onto the surface of the alkylation catalyst. The alkylation catalyst may be exposed to the base for an amount of time ranging from approximately 1 minute to approximately one hour.

Once adsorbed, the alkylation catalyst may be heated to a temperature sufficient to desorb the base from a first portion of the active sites while the base remains adsorbed to a second portion of the active sites. For instance, the base may desorb from the weakly acidic active sites and the intermediate acidity active sites while remaining adsorbed to the strongly acidic active sites. The temperature used to desorb the base from the first portion of the active sites may range from approximately 175° C. to approximately 440° C. The alkylation catalyst may be heated at this temperature for a sufficient amount of time, such as from approximately 15 minutes to approximately two hours, to desorb the base from the first portion of the active sites. Since the base remains adsorbed to the strongly acidic active sites at a temperature greater than or equal to approximately 450° C., the strongly acidic active sites may be selectively poisoned by the base.

The strongly acidic active sites may be selectively poisoned before the alkylation catalyst is used to catalyze the alkylation reaction. For instance, the strongly acidic active sites may be selectively poisoned after the alkylation catalyst is synthesized or purchased. Alternatively, the strongly acidic active sites on the alkylation catalyst may be selectively poisoned after the alkylation catalyst has been used in the alkylation reaction for a predetermined amount of time and has been subsequently regenerated. To poison the strongly acidic active sites, the alkylation catalyst may be taken offline periodically and exposed to the base. The alkylation catalyst may also be selectively poisoned initially, before the alkylation catalyst is first used, and after the alkylation catalyst has been used for a predetermined amount of time and regenerated.

The strongly acidic active sites may also be selectively poisoned by incorporating the base into the regeneration process. A small amount of the base may be dissolved in a supercritical fluid used in the supercritical fluid regeneration process described in the Ginosar '821 patent. For instance, the base may be present in the supercritical fluid at from approximately 0.001 millimole per gram of the alkylation catalyst to approximately 0.1 millimole per gram of the alkylation catalyst.

In another embodiment, the alkylation catalyst may be synthesized or manufactured to include fewer strongly acidic active sites, preventing the condensed hydrocarbon species from forming and accumulating on the alkylation catalyst. For instance, the alkylation catalyst may be synthesized to have a decreased number of strongly acidic active sites. As known in the art, the Si/Al ratio is a measure of the acidity of the alkylation catalyst. By adjusting the Si/Al ratio of the alkylation catalyst and by applying post-synthesis methods, the alkylation catalyst may have a reduced number of strongly acidic active sites upon which the condensed hydrocarbon species form. The Si/Al ratio of the zeolite may range from approximately 2.5 to approximately 15. Zeolites that fall within this range of Si/Al ratio are commercially available, such as from Mallinckrodt Baker, Inc. or Zeolyst International, or may be synthesized by conventional techniques.

The alkylation catalyst may also be manufactured at a temperature that decreases the formation of the strongly acidic active sites. For the sake of example only, if the alkylation catalyst is a commercially available USY zeolite in the ammonium form and is exposed to different calcining temperatures, the number and strength of strongly acidic active sites that form on the alkylation catalyst may differ.

In another embodiment, the alkylation catalyst may have a pore size distribution that hinders the formation of the condensed hydrocarbon species. The alkylation catalyst may include a plurality of pores in which the alkylation reaction occurs. By selecting the size distribution of the pores on the alkylation catalyst to be smaller than the size of the condensed hydrocarbon species, the condensed hydrocarbon species may be sterically constrained from forming on the alkylation catalyst. However, the pore size distribution of the alkylation catalyst may be sufficiently large for the desired product of the alkylation reaction to form. To sterically constrain formation of the condensed hydrocarbon species, the pore size distribution of the alkylation catalyst may range from approximately 5 Å to approximately 8 Å. The size of the pores may be determined as known in the art, such as by estimating the void structure and pore dimensions using conventional nitrogen physisorption measurements.

By modifying the surface of the alkylation catalyst, the formation of the condensed hydrocarbon species on the alkylation catalyst may be reduced or eliminated. Therefore, the alkylation catalyst may be regenerated more efficiently. The alkylation catalyst having the modified surface may be used to catalyze an alkylation reaction in the petroleum industry or in another industry. For the sake of example only, the alkylation catalyst of the present invention may be used to catalyze the reaction between a paraffin and an olefin to produce an alkylation product, as described in U.S. Pat. No. 6,103,948 to Ginosar et al. (the "Ginosar '948 patent"), the disclosure of which is incorporated by reference herein. The paraffin may be a compound that includes from 4 to 8 carbon atoms, such as isobutane, isopentane, 3-methylhexane, 2-methylhexane, 2,3-dimethylbutane, 2,4-dimethylhexane, analogs thereof, or mixtures thereof. The olefin may be a compound having from 2 to 12 carbon atoms, such as 2-butene, 1-butene, isobutylene, propylene, ethylene, hexene, octene, heptene, or homologs thereof. In one embodiment, the paraffin is isobutane and the olefin is 2-butene.

During the alkylation reaction, the hydrocarbon species may adsorb onto the active sites of the alkylation catalyst in the form of carbocations. As used herein, the term "carbocation" refers to a positively charged carbonaceous compound and also refers to a surface alkoxide. The hydrocarbon species formed during the alkylation reaction may include hydrocarbons that have low volatility and high molar mass. The hydrocarbon species may be produced by side reactions during the alkylation reaction or may be introduced with the paraffin or olefin reactants. As the hydrocarbon species accumulate on the alkylation catalyst, the number of active sites available to catalyze further reactions may decrease, deactivating the alkylation catalyst and reducing its efficiency. However, since the alkylation catalyst has the modified surface, the formation of the condensed hydrocarbon species on the alkylation catalyst may be reduced or eliminated during at least one of the alkylation reaction and the regeneration of the alkylation catalyst.

As the alkylation reaction is performed, the alkylation catalyst may become partially deactivated or substantially completely deactivated by the hydrocarbon species. However, since the formation of the condensed hydrocarbon species is reduced or eliminated by the modified surface of the alkylation catalyst, regeneration of the alkylation catalyst may be more efficient. In other words, the alkylation catalyst may be substantially completely regenerated using the supercritical fluid regeneration process described in the Ginosar '821 patent. Therefore, the alkylation reaction may also be allowed to proceed for longer amounts of time before regeneration of the alkylation catalyst is necessary. In addition, when regeneration is needed, the regeneration may be performed more quickly. During the regeneration process, the formation of additional condensed hydrocarbon species on the alkylation catalyst may also be reduced or eliminated due to the modified surface of the alkylation catalyst.

Other regeneration processes known in the art may also be used to regenerate the alkylation catalyst. For instance, the alkylation catalyst may be regenerated by oxidizing carbonaceous species in air or oxygen. However, since the oxidation process may decompose the base that is adsorbed to the alkylation catalyst, additional base may be adsorbed onto the alkylation catalyst, as previously described, before re-using the alkylation catalyst. Alkylation catalysts may be regenerated by hydrogenating the carbonaceous species, allowing their desorption from the surface of the alkylation catalyst.

In contrast, if the alkylation catalyst used in the alkylation reaction is a solid alkylation catalyst that does not have its surface modified as described above, the hydrocarbon species and the condensed hydrocarbon species may form during the alkylation reaction. The amount of the hydrocarbon species and the condensed hydrocarbon species that form on the alkylation catalyst may depend on an amount of time that the alkylation reaction is allowed to proceed before regenerating the alkylation catalyst, the paraffin/olefin feed ratio, the olefin weight hourly space velocity ("OWHSV"), and the alkylation temperature. The condensed hydrocarbon species may begin to form on the unmodified alkylation catalyst as the alkylation reaction proceeds for longer amounts of time. For instance, if the alkylation reaction proceeds for approximately 1 hour to approximately 3 hours, the condensed hydrocarbon species may be present on the unmodified alkylation catalyst in small amounts and any deactivation of the unmodified alkylation catalyst may be substantially due to the presence of the hydrocarbon species. The hydrocarbon species may form on the unmodified alkylation catalyst when the unmodified alkylation catalyst has been contacted with up to approximately 3 grams of olefin per gram of catalyst per hour. In contrast, if the alkylation reaction proceeds for longer amounts of time, such as from approximately 6 hours to approximately 8 hours, larger amounts of the condensed hydrocarbon species may form on the unmodified alkylation catalyst. The condensed hydrocarbon species may form on the unmodified alkylation catalyst when the unmodified alkylation catalyst has been contacted with greater than approximately 3 grams of olefin per gram of catalyst per hour. As such, after longer reaction times, the unmodified alkylation catalyst may be deactivated by both the hydrocarbon species and the condensed hydrocarbon species.

As previously described, the condensed hydrocarbon species may include unsaturated hydrocarbon species that are produced during the alkylation reaction. While regeneration of the unmodified alkylation catalyst may effectively remove a majority of the hydrocarbon species, a portion of the hydrocarbon species may remain on the unmodified alkylation catalyst. In addition, the condensed hydrocarbon species or unsaturated hydrocarbon species may remain on the unmodified alkylation catalyst. Additional condensed hydrocarbon species may also form on the unmodified alkylation catalyst during the regeneration because the hydrocarbon species remaining on the unmodified alkylation catalyst may dehydrogenate rather than being extracted by the supercritical fluid. For instance, aromatic hydrocarbons, polycyclic hydrocarbons, graphitic coke compounds, or mixtures thereof on the unmodified alkylation catalyst may be formed during the supercritical fluid regeneration.

On the unmodified alkylation catalyst, the supercritical fluid regeneration may be less than 100% effective because the condensed hydrocarbon species remain after the regeneration. In order to achieve 100% effectiveness of the supercritical fluid regeneration on the unmodified alkylation catalyst, the reaction time of the alkylation reaction may be substantially reduced so that the condensed hydrocarbon species do not form on the alkylation catalyst. However, if the alkylation catalyst having the modified surface is used, the alkylation reaction may be performed for longer periods of time and the supercritical fluid regeneration may be substantially 100% effective.

The following examples serve to explain embodiments of the present invention in more detail. These examples are not to be construed as being exhaustive or exclusive as to the scope of this invention.

EXAMPLES

Example 1

Characterization of Hydrocarbon Species Remaining on an USY Zeolite Before and after Supercritical Fluid Regeneration The chemical nature of hydrocarbons remaining on an USY zeolite before and after supercritical isobutane regeneration ("SFR") at 453 K and $1.1 \times 10^7$ Pa was determined. The USY zeolite was utilized for a liquid phase isobutane/butene alkylation reaction at 333 K and $1.1 \times 10^7$ Pa. Samples of the USY zeolite were deactivated to different levels by running the alkylation reaction for different times on stream ("TOS") and regenerated under flowing supercritical isobutane for 60 minutes.

Experimental

A precursor for the alkylation catalyst was the ammonium form of the USY zeolite (CBV-500 from Zeolyst International, Si/Al=2.6). The USY zeolite was pelletized, crushed, and sieved, and the fraction between 8 and 20 ASTM mesh was collected and calcined at 823 K for 3 hours to obtain the acid form of the alkylation catalyst.

A continuous flow reaction/regeneration experimental system that included a stainless steel tube reactor housed in an electrically heated aluminum block, high pressure feed pumps, a recycle pump, and an on-line gas chromatograph ("GC") was employed. The reactor dimensions were approximately 44 cm in length by 8 mm internal diameter ("i.d."). The fluids were preheated in a tubing coil before entering the reactor. For the reaction step, the reactor was operated in partial recycle mode with the aid of a turbo-micropump (Micropump, Inc. IDEX Co.), while the regeneration step was operated in a single pass mode. An ISCO model 260D high pressure syringe pump was employed to pump the reactants, which included a premixed 20:1 molar ratio of isobutane/2-butene feed, for the reaction step. Typical fresh feed molar composition as determined by GC analysis was: isobutane 94.75%, trans 2-butene 2.83%, and cis 2-butene 2.06%. The only detected impurities were propane (0.20%) and n-butane (0.16%). The fresh feed and recycle flow rates were 2.5 $cm^3$/minute and 50 $cm^3$/minute, respectively. A second ISCO model 260D high-pressure syringe pump was used to supply isobutane both to pressurize the system before reaction and to regenerate the catalyst. Impurities in the isobutane stream included propane 0.23% and n-butane 0.29%. GC detection of the reactor effluent was performed on-line using a Hewlett Packard 5890 Series II Gas Chromatograph equipped with an automated high-pressure sampling valve, a flame ionization detector ("FID") and a 50 m×0.2 mm (1×i.d.) Supelco Petrocol column. The GC oven temperature was held initially at 323 K for 5 minutes, ramped to 423 K at 10 K/minute, and held at 423 K for 0.5 minute.

Two sets of experiments were performed. The first set consisted of a reaction step only, while the second set consisted of a reaction step followed by a regeneration step. For each experiment, eight grams of the acid form of the USY zeolite was loaded in the reactor and pretreated overnight in situ at 473 K under flowing helium. The temperature was then decreased to 333 K and the system pressurized at $1.1 \times 10^7$ Pa with isobutane. At time zero, the flow of reactants (i.e., a mixture of the isobutane/2-butene feed) was initiated at a flow rate necessary to achieve an OWHSV of 0.5 g butene/(g catalyst×h). Samples of the product stream during reaction were analyzed by GC every 20 minutes. The experimental setup did not allow for product stream sampling during regeneration.

For the reaction-only experiments, after the pre-selected TOS (60 minutes, 180 minutes, 280 minutes, and 380 minutes) had elapsed, the reactant flow was stopped, the system cooled down to room temperature, flushed with helium at $3.4 \times 10^6$ Pa for 2 hours, and the USY zeolite was recovered. About 0.5 $cm^3$ of the catalyst bed recovered from the reactor inlet, which usually presented a color slightly different than the rest of the catalyst bed and was contaminated with quartz wool particles from the inlet quartz wool plug, was discarded. The rest of the reactor content was mixed and used in subsequent analyses. These samples were assumed to represent the catalyst conditions before regeneration.

For the reaction/regeneration experiments, after the pre-selected TOS (60 minutes, 180 minutes, 270 minutes, and 360 minutes) had elapsed, the reactant flow was stopped, and 2 ml/minutes of isobutane at $1.1 \times 10^7$ Pa was flowed through the reactor, the temperature was increased to 453 K over a period of 30 minutes to achieve supercritical conditions and maintained at 453 K for 60 minutes to regenerate the USY zeolite. Finally, the system was cooled down, flushed, and the USY zeolite recovered following the same procedure as described for the reaction-only experiments.

Nitrogen physisorption measurements were performed on an automated Quantachrome Autosorb-1C system. To minimize changes in the amount and nature of carbonaceous species retained on the surface of the USY zeolite, pretreatment of samples for nitrogen physisorption measurements included outgassing at 298 K for 3 hours. Special care was taken to avoid sample exposure to environmental moisture before conducting any analysis including nitrogen physisorption measurements. The fresh USY zeolite sample was submitted to the same protocol as the USY zeolites samples loaded in the reactor (i.e., overnight treatment in flowing helium at 473 K and outgassing at 298 K for 3 hours afterwards). B.E.T. surface areas were calculated in the range of P/Po between 0.05 and 0.10 and micropore volume was determined by the t-plot method, as known in the art.

Temperature programmed oxidation ("TPO") and temperature programmed desorption ("TPD") measurements were performed on a Perkin Elmer Diamond TG/DTA microbalance under 100 ml/minute flowing air and nitrogen, respectively. Typically, 10 mg of sample were placed in the balance pan and heated at 10 K/minute from room temperature to 373 K. The temperature was maintained at 373 K for 30 minutes to allow for water desorption, and then increased to 1073 K at 10 K/minute. The change in weight was recorded and the negative of its derivative with respect to time utilized to report TPO and TPD profiles. Because zeolites are able to retain water even at temperatures as high as 773 K, it is not possible to completely rule out a minimal contribution of water to the weight changes in the thermogravimetric analysis. However, continuous monitoring of the TPO or TPD product stream by quadrupole mass spectrometry revealed that m/e=17 and 18 signals, which correspond to water, remained at baseline levels above 373 K in all experiments. Thus, it was assumed that all water desorbed at or below 373 K and the amount of hydrocarbons desorbed was calculated from the change in weight with respect to the sample weight after water desorption.

Diffuse reflectance infrared Fourier transform spectroscopy ("DRIFTS") studies were performed at room temperature on a Nicolet Magna 750 Fourier transform infrared spectrometer equipped with a commercial Spectratech diffuse reflectance cell. Eight-hundred-scan spectra were collected in the 4000-400 $cm^{-1}$ range at a resolution of 4 $cm^{-1}$. Ultraviolet-visible ("UV-Vis") diffuse reflectance spectroscopy measurements were carried out on a Shimadzu UV-3101 PC scanning spectrophotometer equipped with an integrating sphere attachment. A small amount of powder USY zeolite sample was placed on paper and spectra collected in the 700-250 nm wavelength range.

USY Zeolite Deactivation Profile

Figure 2:
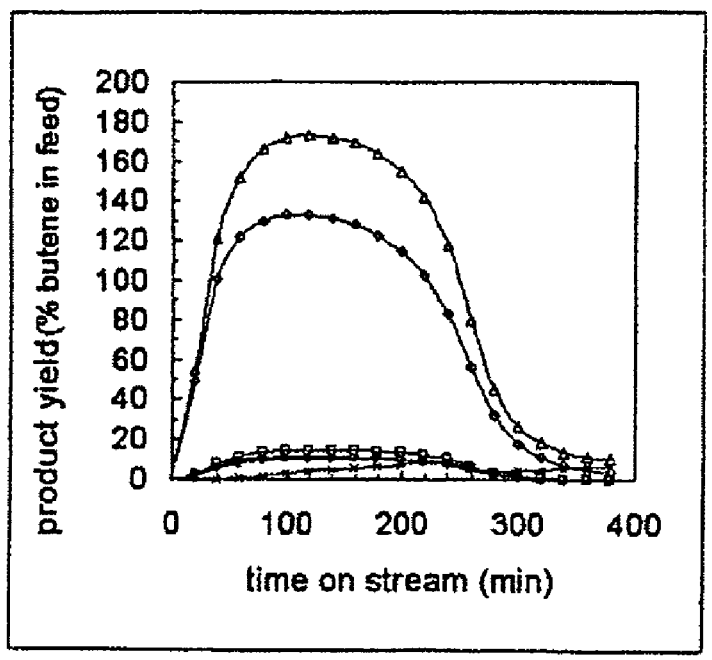
FIG. 2 shows a plot of product yield as a function of time on stream (total products $C_5$ and above (Δ), octanes (◊), pentanes (□), hexanes (○), heptanes (+), and total $C_9$ and above (X))
Figure 3:
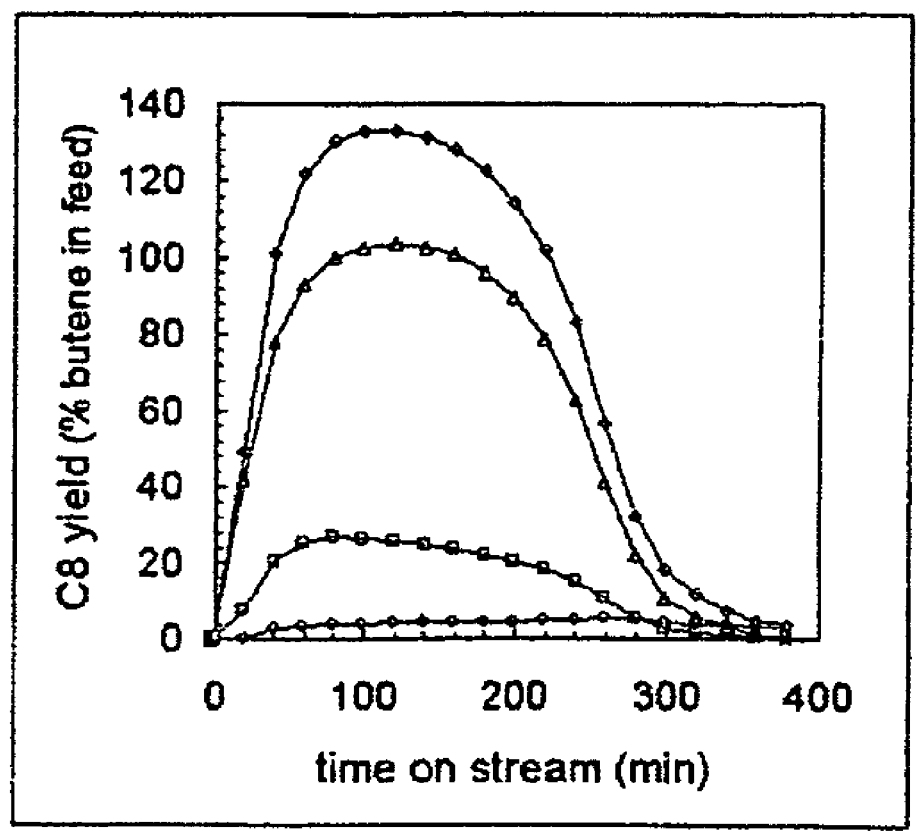
FIG. 3 shows a plot of $C_8$ yield in a product stream as a function of time on stream (total octanes (◊), trimethylpentanes (Δ), dimethylhexanes (□), and other C8 hydrocarbons (○))

Since a partially deactivated catalyst can be regenerated completely but a totally deactivated catalyst is less than fully regenerated, the effectiveness of the SFR process was expected to depend on the degree of deactivation of the USY zeolite. A set of preliminary experiments was performed to determine TOSs at which to stop the reaction and start the SFR process, in order to have samples that represented the complete deactivation profile of the USY zeolite. Typical results obtained for USY zeolite activity and selectivity are shown in FIGS. 1-3. Catalyst activity as measured by butene conversion is shown in FIG. 1. Catalyst activity was measured by butene conversion. For the first 120 minutes of TOS, butene was converted completely. In other words, butene was not detected in the fluid phase leaving the reactor. Between 120 minutes and 240 minutes, conversion decreased to about 90% and, after 240 minutes, a pronounced decrease was apparent. Trimethylpentane ("TMP") production reached a maximum at around 120 minutes TOS and was insignificant after 360 minutes TOS, as shown in FIGS. 2 and 3. Distinct stages have been reported to occur in the deactivation profile of alkylation catalysts: (i) the initial activity at time zero, which is difficult to observe; (ii) the useful lifetime of the catalyst, characterized by high conversion and slow deactivation; (iii) the rapid deactivation, characterized by a fast decrease of activity along with a change in selectivity to $C_{9+}$ products; and (iv) the last stage, where catalyst deactivation is again slow and the products are primarily $C_{9+}$ products. The $C_{5+}$ product composition in the second stage is mostly $C_8$ isoparaffins due to alkylation activity, along with some production of $C_5$-$C_7$, which indicates cracking of olefin oligomers. During the third stage, activity for alkylation and cracking decrease while oligomerization is maintained. The products during the last stage are mainly $C_{9+}$ that arise primarily from olefin oligomerization.

After considering the activity and selectivity profiles shown in FIGS. 1-3, TOSs of 60 minutes, 180 minutes, 280 minutes, and ca. 380 minutes were selected to stop the reaction and perform the regeneration step. As used herein, samples before regeneration are denoted as 0, 60, 180, 280, and 380; and after regeneration as 0R, 60R, 180R, 280R, and 360R. The numbers indicate the TOS spent under alkylation reaction.

USY Zeolite Characterization

The results of nitrogen physisorption measurements performed on the USY zeolite samples before regeneration are shown in Table 1.

TABLE 1

USY Zeolite Surface Area and Micropore Volume before SFR.

| | Sample | | | | | |
|---|---|---|---|---|---|---|
| | Fresh | 0 | 60 | 180 | 280 | 380 |
| B.E.T. surface area ($m^2/g$) | 768 | 758 | 498 | 287 | 106 | 107 |
| Micropore volume ($cm^3/g$) | 0.28 | 0.23 | 0.14 | 0.06 | 0.005 | 0.000 |

Results for both fresh and blank experiment samples (i.e., sample 0) are also included for comparison purposes. Note that fresh sample in Table 1 denotes the acid form of the USY zeolite after overnight pretreatment at 473 K under flowing helium and that sample 0 indicates a sample recovered just after pressurizing the system with isobutane and without contacting any reactant mixture. When compared to the fresh USY zeolite, all spent samples showed lower surface area and micropore volume, and the loss in surface area and micropore volume increased with TOS. Micropore volume was negligible in sample 280 and below detection limit in sample 380, which indicated a completely filled/blocked micropore system for a fully deactivated catalyst.

Table 2 shows the results of nitrogen physisorption measurements on USY zeolite samples submitted to SFR for 60 minutes at 453 K.

TABLE 2

Catalyst surface area and micropore volume after SFR.

| | Sample | | | | |
|---|---|---|---|---|---|
| | 0R | 60R | 180R | 280R | 360R |
| B.E.T. surface area ($m^2/g$) | 748 | 705 | 698 | 722 | 645 |

TABLE 2-continued

Catalyst surface area and micropore volume after SFR.

| | Sample | | | | |
|---|---|---|---|---|---|
| | 0R | 60R | 180R | 280R | 360R |
| Micropore volume (cm³/g) | 0.24 | 0.23 | 0.23 | 0.23 | 0.24 |

Data for a blank experiment (0R) sample is also included for comparison purposes. In this case, the blank experiment included pressurizing the system with isobutane at reaction temperature, increasing the temperature to SFR conditions, and flowing supercritical isobutane for 60 minutes. From Table 2, it is apparent that the SFR process produced a significant recovery in sample surface area and micropore volume, above 80% with respect to the fresh catalyst sample.

Characterization of Adsorbed Hydrocarbons

Examples of TPO and TPD determinations performed on samples before and after SFR are shown in FIGS. 4-7. TPO experiments run on samples before SFR (curves 60 to 380 in FIG. 4) revealed two differentiated peaks. The first one, positioned between 373 K and 573 K, was assigned to the release of low molecular weight hydrocarbons, and the second one, between 573 K and 923 K, was attributed to $CO_2$ produced by oxidation of adsorbed hydrocarbons. These assignments were confirmed by mass spectrometric analysis of the gaseous stream. Only the low temperature (first) peak was seen on the TPO profile of the blank experiment sample (curve 0 in FIG. 4). TPD under flowing nitrogen (FIG. 5) revealed desorption of hydrocarbons up to about 673 K. Both, TPD and low temperature TPO peaks displayed maxima that shifted to higher temperatures with TOS, i.e., from around 425 K (sample 60) to 480 K (sample 380). The presence of shoulders on the TPD peaks indicated desorption of a larger variety of hydrocarbons at higher temperatures.

Figure 6:
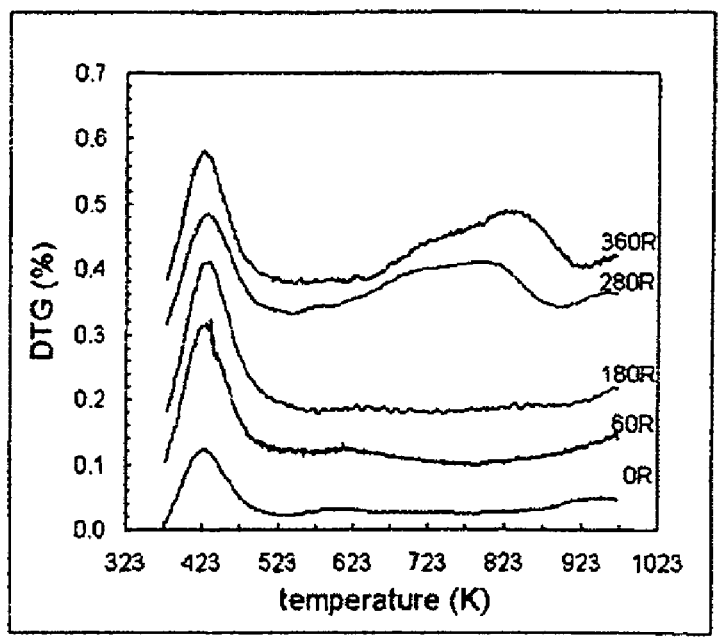
FIG. 6 shows a TPO plot of USY zeolite samples after SFR.
Figure 7:
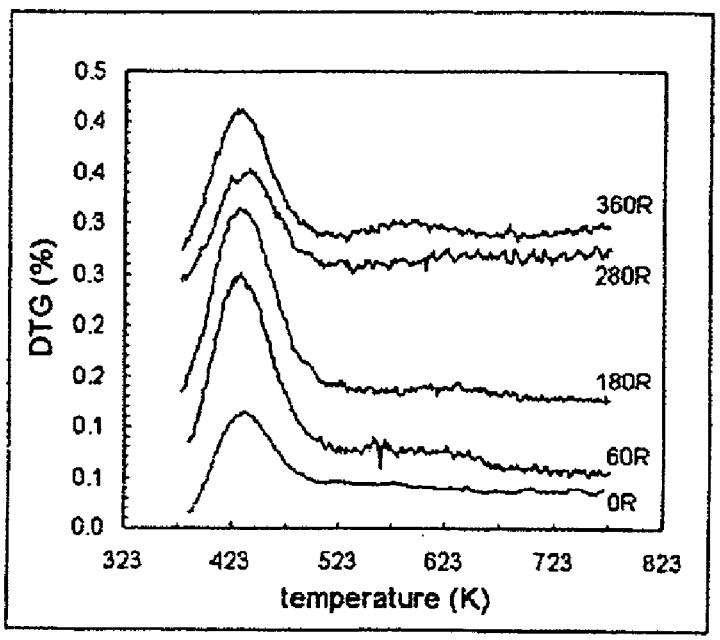
FIG. 7 shows a TPD plot of USY zeolite samples after SFR.

FIGS. 6 and 7 show TPO and TPD profiles obtained from samples submitted to SFR. Carbon dioxide produced by TPO was found only from samples submitted to the two longest TOS (curves 280R and 360R in FIG. 6). The first TPO peak maxima were observed at ca. 425 K-430 K regardless of TOS.

Quantitative data for the amount of hydrocarbon species desorbed by TPO and TPD from all samples are summarized in Tables 3 and 4. The total content of hydrocarbons measured on samples before SFR increased with TOS and ranged from 0.9% (sample 0) to 16.3% (sample 380). Although after SFR (Table 4) the total amount of adsorbed hydrocarbons increased also with TOS, no detectable amount of $CO_2$ was produced from either sample 60R or 180R. Samples 280R and 360R exhibited a lower amount of hydrocarbons desorbing as the first peak and around 3.1% and 3.3% that was removed as $CO_2$, respectively. Most of the hydrocarbons present on samples 280R and 360R desorbed as $CO_2$; in other words, more than 60% of the total desorption corresponded to the second TPO peak.

TABLE 3

Average Hydrocarbon Content before SFR as determined by TPD and TPO Measurements (n.d. stands for not detected).

| | Sample | | | | |
|---|---|---|---|---|---|
| Min TOS | 0 | 60 | 180 | 280 | 380 |
| TPO (wt %) | | | | | |
| Hydrocarbon desorbed below 573 K | 0.9 | 5.1 | 6.5 | 6.0 | 7.2 |
| Hydrocarbons removed as $CO_2$ | n.d. | 4.0 | 6.0 | 9.0 | 9.1 |
| Total | 0.9 | 9.1 | 12.5 | 15.0 | 16.3 |
| TPD (wt %) | | | | | |
| Hydrocarbons desorbed below 673 K | 0.9 | 8.5 | 11.2 | 11.1 | 12.5 |

TABLE 4

Average Hydrocarbon Content after SFR as determined by TPD and TPO Measurements (n.d. stands for not detected).

| | Sample | | | | |
|---|---|---|---|---|---|
| Min TOS | 0R | 60R | 180R | 280R | 360R |
| TPO (wt %) | | | | | |
| Hydrocarbon desorbed below 573 K | 1.2 | 2.7 | 2.7 | 1.7 | 1.9 |
| Hydrocarbons removed as $CO_2$ | n.d | n.d. | n.d. | 3.1 | 3.3 |
| Total | 1.2 | 2.7 | 2.7 | 4.8 | 5.2 |
| TPD (wt %) | | | | | |
| Hydrocarbons desorbed below 673 K | 1.2 | 2.8 | 2.7 | 1.7 | 1.8 |

DRIFTS Analysis

FIGS. 8A and 8B and FIGS. 9A and 9B show the DRIFTS spectra of samples before and after SFR, respectively. For hydrocarbons species, the CH stretching region generally spans from 2700 $cm^{-1}$ to 3100 $cm^{-1}$, and the CC stretching vibrations and the CH deformation vibrations are below 1650 $cm^{-1}$ and 1465 $cm^{-1}$, respectively. For Y zeolites, bands at ca. 3745 $cm^{-1}$, 3640 $cm^{-1}$, and 3540 $cm^{-1}$ are usually assigned to external terminal silanol groups, hydroxyl groups of the supercages, and hydroxyl groups of the β-cages, respectively. Peaks that correspond to skeletal vibrations of the zeolite framework are below -about 1500 $cm^{-1}$ and envelop some of the low frequency hydrocarbon vibrations on the spectra of hydrocarbons adsorbed on zeolites.

The DRIFTS spectrum of the fresh USY zeolite (FIG. 8A) showed the characteristic silanol and acidic OH stretching signals between 3500 $cm^{-1}$ and 3800 $cm^{-1}$. More specifically, the silanol peak is revealed at 3743 $cm^{-1}$, and the supercage and β-cage hydroxyl group peaks are seen at 3670 $cm^{-1}$ and 3588 $cm^{-1}$, respectively. All spectra of samples submitted to reaction (i.e., 60 to 380 on FIG. 8A) displayed CH stretching bands between 2800 $cm^{-1}$ and 3000 $cm^{-1}$, in which the contribution of the $v_{as}CH_3$ peak at 2963 $cm^{-1}$ was very important and the relative contribution of $v_{as}CH_2$ (aliphatic) at 2937 cm$^{-1}$ increased with TOS. At the same time, the hydroxyl band at 3670 cm$^{-1}$ decreased with TOS. Analyzing the spectra on the CC stretching and CH deformation region (FIG. 8B), a band at ca. 1635 cm$^{-1}$ is present in all spectra. Bands around 1635 cm$^{-1}$ are usually assigned to C=C stretching, but water also absorbs infrared radiation at that frequency. Two more bands, ca. 1470 cm$^{-1}$ and 1367 cm$^{-1}$, which may be assigned to CH deformation of $CH_2$ and $CH_3$ groups, are also seen on the spectra of samples submitted to reaction (curves 60 to 280).

Figure 8A:
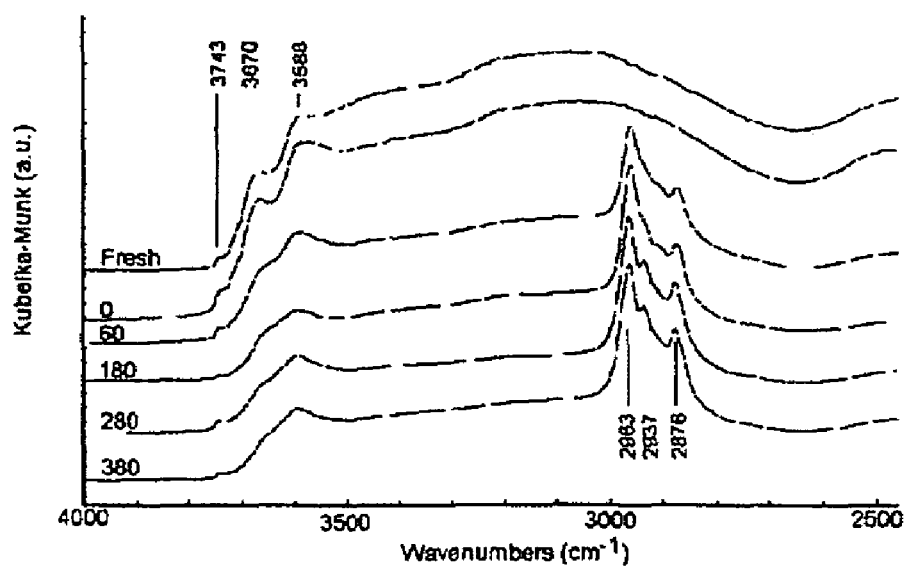
FIG. 8A shows Diffuse Reflectance Infrared Fourier Transform Spectroscopy ("DRIFTS") spectra in the CH and OH stretching region of USY zeolite samples before SFR.
Figure 8B:
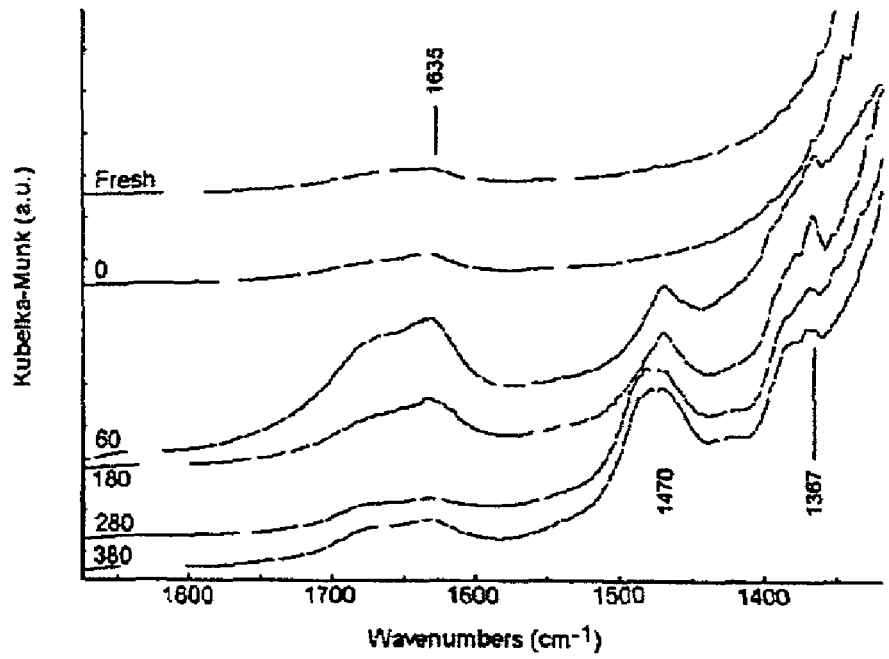
FIG. 8B shows DRIFTS spectra in the CC stretching and CH deformation region of USY zeolite samples before SFR.
Figure 9A:
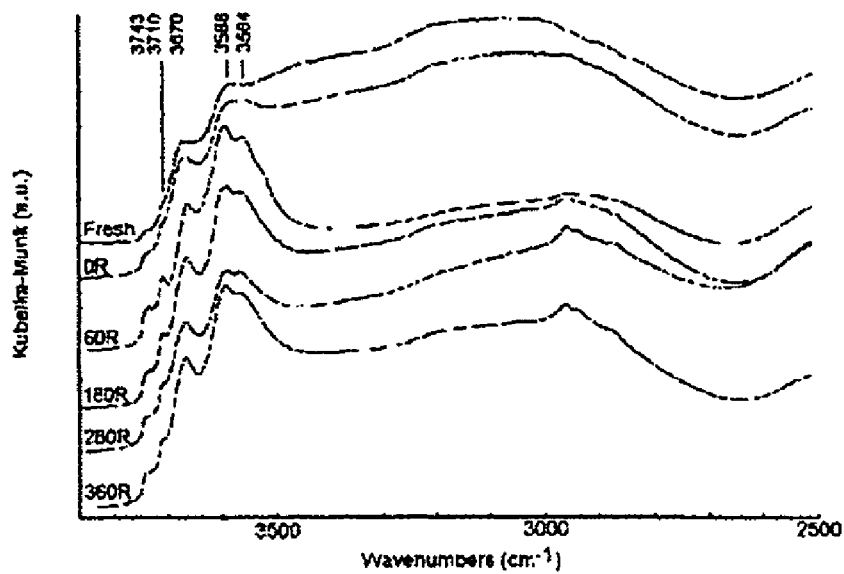
FIG. 9A shows DRIFTS spectra in the CH and OH stretching region of USY zeolite samples after SFR.
Figure 9B:
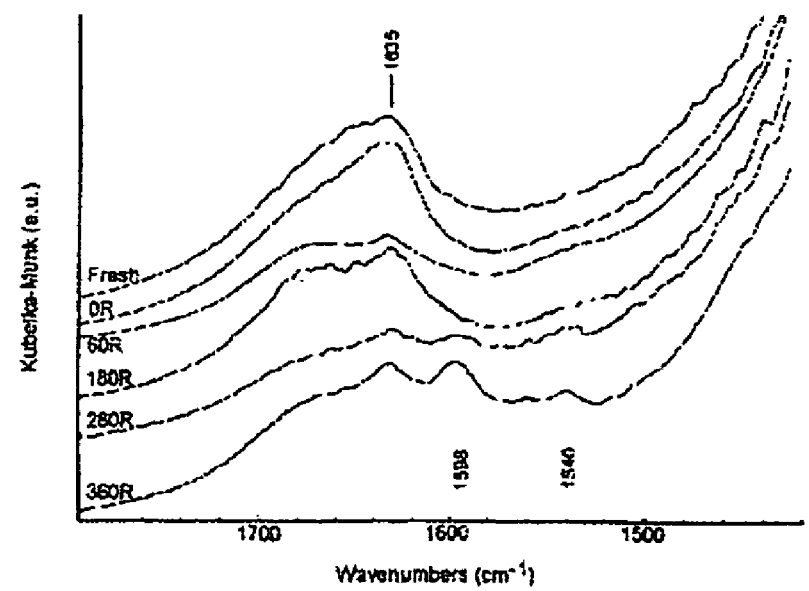
FIG. 9B shows DRIFTS spectra in the CC stretching and CH deformation region of USY zeolite samples after SFR.

FIGS. 9A and 9B show the DRIFTS spectra of samples after SFR. Spectra of regenerated samples (i.e., 60R-360R) displayed at least five peaks in the silanol-hydroxyl region (FIG. 9A). Comparing with spectra of samples taken before SFR (FIG. 8A), an improved definition of the peak corresponding to supercage hydroxyl groups (3670 cm$^{-1}$) along with peaks at 3710 cm$^{-1}$ and 3564 cm$^{-1}$ was seen on all regenerated sample spectra. Low intensity CH stretching components between 2800 cm$^{-1}$ and 3000 cm$^{-1}$ are displayed by samples 180R, 280R, and 360R. A band ca. 1635 cm$^{-1}$ (FIG. 9B) was found in all spectra and small peaks at 1540 cm$^{-1}$ and 1598 cm$^{-1}$ on the spectra of samples 280R and 360R. Bands around 1540 cm$^{-1}$ are ascribed to alkylnaphthalenes or polyphenylene structures, and around 1580 cm$^{-1}$ to 1610 cm$^{-1}$ to complex mixtures of hydrogen-deficient carbonaceous deposits. It is worth noting that none of the regenerated samples displayed spectra with CH deformation bands around 1470 cm$^{-1}$ or 1370 cm$^{-1}$ (region not shown), as they did before SFR.

UV/Vis Analysis

Figure 10:
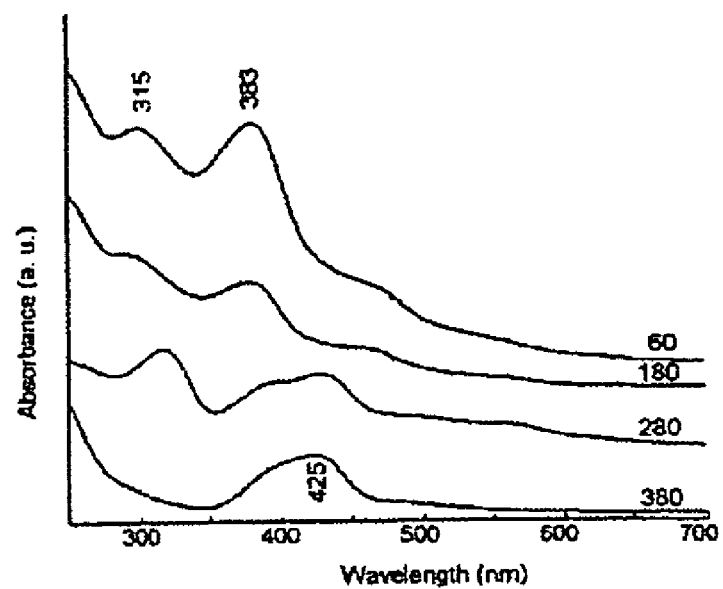
FIG. 10 shows Ultraviolet-visible ("UV-Vis") spectra of USY zeolite samples before SFR.
Figure 11:
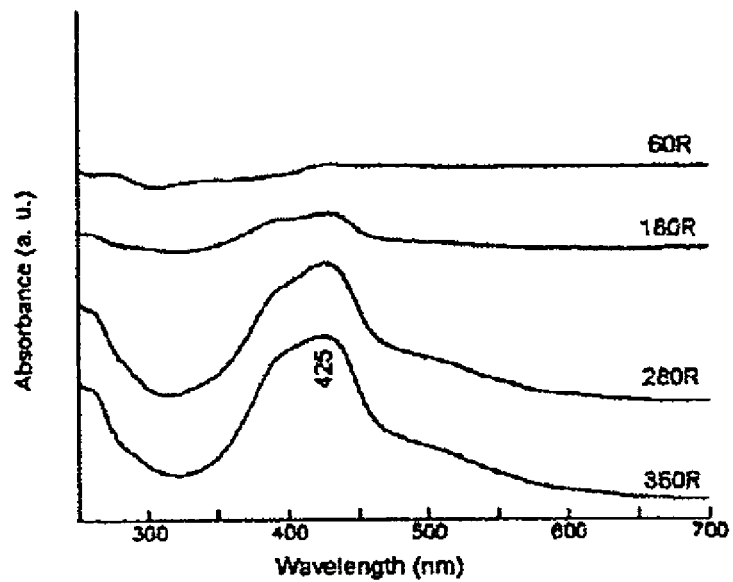
FIG. 11 shows UV-Vis spectra of USY zeolite samples after SFR.

Bands on UV-Vis spectra generally indicate the presence of unsaturated species. Particularly, allylic, dienylic, and polyenylic carbocations have been reported to absorb UV-Vis radiation between 290 nm-345 nm, 370 nm-390 nm, and 430 nm-490 nm, respectively; and polycyclic aromatic compounds around 410 nm. UV-Vis diffuse reflectance absorption spectra of samples before and after SFR are shown in FIGS. 10 and 11, respectively. Before SFR, at least monoenylic (315 nm) and dienylic (383 nm) carbocations were detected on samples submitted to reaction up to 280 minutes TOS (FIG. 10). The 280 minutes TOS sample also displayed spectrum features that may be assigned to polycyclic aromatic compounds (broad band around 425 nm) and the 380 minutes TOS sample showed mostly polycyclic aromatic compounds.

After SFR (FIG. 11), bands around 425 nm assigned to polycyclic aromatic compounds were apparent on the spectra of samples regenerated after reacting for 180 or more minutes TOS (curves 180R, 280R, and 360R in FIG. 11). It is worth mentioning that neither sample 0 nor 0R displayed any UV-Vis absorption band that could correspond to unsaturated carbocations.

Results

The general decrease in nitrogen physisorption capacity and, particularly, the decrease in micropore volume with TOS of all samples before regeneration (Table 1) indicated that hydrocarbon species were adsorbed on the internal channels of the zeolite catalyst. A shift of the zeolite lattice vibration band, centered around 1308 cm$^{-1}$ on the fresh sample spectrum (not shown), to lower wavenumbers (i.e., 1270 cm$^{-1}$) was found on the DRIFTS spectra of all samples before SFR. By submitting those samples to outgassing, the intensity of all hydrocarbon bands decreased and the zeolite lattice vibration peak returned to 1308 cm$^{-1}$. That shift confirmed that hydrocarbon species were located inside the zeolite channels. The shift of the first TPO peak to higher temperatures and the TPD peak, which became broader and revealed shoulders, with TOS (FIGS. 4 and 5) indicated an increase of both molecular weight and diversity of adsorbed species as the USY zeolite deactivated.

Comparing Table 2 with Table 1, it is apparent that the SFR process was effective in recovering most of the surface area and micropore volume. Sample micropore volumes after SFR resembled the micropore volume of the blank experiment sample before regeneration (sample 0). Both 0 and 0R samples displayed nitrogen physisorption capacity, particularly micropore volumes, lower than the fresh sample. This decrease may be attributed to the retention in the zeolite pores of hydrocarbon species that may have been formed from isobutane and/or undetected unsaturated impurities. In addition, TPO and TPD measurements (i.e., curves 0 in FIGS. 4 and 5 and 0R in FIGS. 6 and 7) confirmed the presence of hydrocarbons in both blank samples.

When correlating the relative loss of nitrogen physisorption capacity (Table 1) with the amount of hydrocarbons deposited on the zeolite pores as measured by TPO (Table 3), a somewhat direct correspondence is found for samples before regeneration. However, no obvious correspondence between nitrogen physisorption capacity and amount of adsorbed hydrocarbons was noticeable after SFR. Nevertheless, the amount of hydrocarbons adsorbed on the zeolite pores after SFR was relatively small when compared with the amount before SFR. It is interesting to note that although samples 360R and 0R presented similar micropore volumes, their hydrocarbon content was different, i.e., 5.2% and 1.2% respectively. Assuming a conservative case scenario, where the carbonaceous deposits are as bulky as the 2,2,4-TMP whose density is 0.8 cm$^3$/g, 1.2% and 5.2% would correspond to a volume of 0.0096 cm$^3$ and 0.0416 cm$^3$ per gram of sample, respectively. Then, instead of 0.24 cm$^3$/g, the expected micropore volume for sample 360R would have been around 0.20 cm$^3$. Two reasons for this discrepancy may be the outgassing before nitrogen physisorption measurements, which may have removed part of the adsorbed species, and the fact that species more condensed (360R) occupy less volume.

It has been reported that the $CO_2$ peak in the TPO of deactivated zeolite alkylation catalysts arises from hydrocarbon restructuring from aliphatic to aromatic during TPO heating. The absence of such a $CO_2$ peak in the TPO profile of samples 0R, 60R, and 180R (FIG. 6 and Table 4) may indicate that the hydrocarbon species remaining after SFR are not exactly precursors of high temperature desorbing hydrocarbons and instead of restructuring they were completely removed at low temperature during the TPO experiment. Before SFR, the only sample that displayed one TPO peak was the blank experiment sample. After SFR, not only the 0R but also the 60R and 180R samples displayed only the low temperature TPO peak, which in general was neither shifted to higher temperatures nor broadened with TOS. In general, for samples 280R and 360R, the amount of low temperature desorbing hydrocarbons removed by TPO and the total hydrocarbons desorbed by TPD coincided, suggesting that no important amount of low temperature desorbing hydrocarbons underwent restructuring toward more condensed forms and that the $CO_2$ peaks were actually produced by deposits already hydrogen deficient after SFR.

One might hypothesize that the SFR process extracted most coke precursors from samples that were regenerated while in their useful catalyst lifetime and that only weakly adsorbed low molecular weight species remained in the zeolite pores after SFR. In contrast, when regeneration was initiated after the USY zeolite was at later stages of deactivation, the amount of high temperature desorbing hydrocarbons changed from 9.0% and 9.1% (samples 280 and 360) to 3.1% and 3.3% (samples 280R and 360R), which accounts for the supercritical extraction of only around 65% of the high temperature desorbing hydrocarbons.

Figure 4:
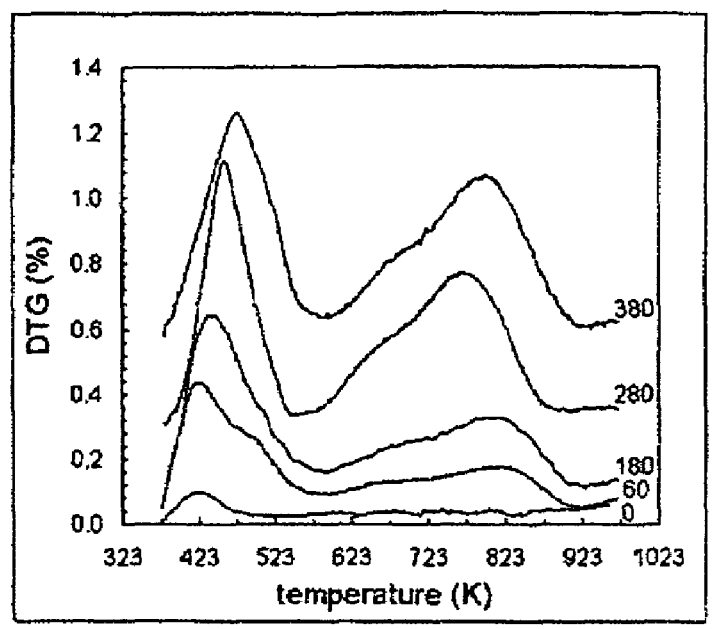
FIG. 4 shows a temperature programmed oxidation ("TPO") plot of USY zeolite samples before supercritical fluid regeneration ("SFR")
Figure 5:
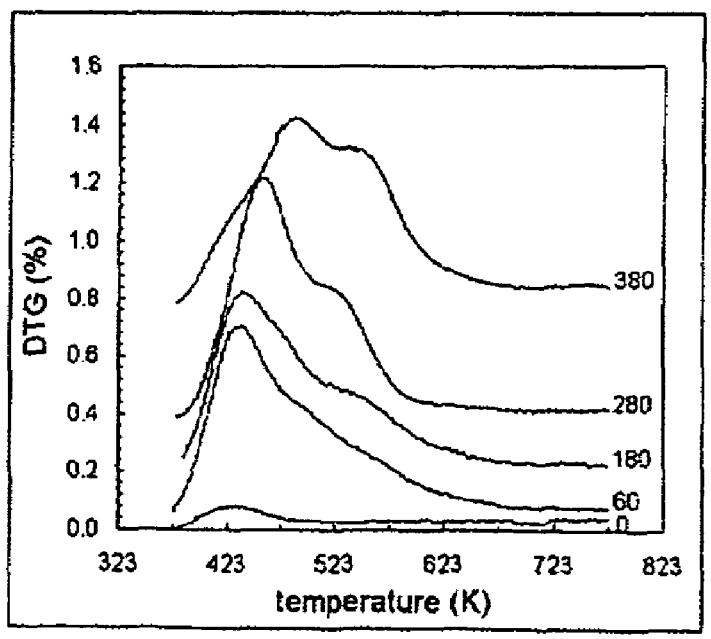
FIG. 5 shows a temperature programmed desorption ("TPD") of USY zeolite samples before SFR.

For samples submitted only to the reaction (curves 60 to 380 in FIG. 8A), the diminished intensity of the hydroxyl band at 3670 cm$^{-1}$ suggests that such acid sites interact with hydrocarbon species and that the deposits are located mainly in the supercages of the zeolite structure. The bands at 2800 cm$^{-1}$ to 3000 cm$^{-1}$ show the highly branched nature of the aliphatic species adsorbed on the zeolite surface, because of the relative high intensity of the $v_{as}CH_3$ peak at 2963 cm$^{-1}$. Moreover, the relatively larger contribution of the $v_{as}CH_2$ (aliphatic) at 2937 cm$^{-1}$ at longer TOS with respect to the peak at 2963 cm$^{-1}$ would indicate an increase of hydrocarbon chain length with TOS in agreement with TPO profiles that indicated an increase in molecular weight of adsorbed species with TOS (FIG. 4).

Although the band at 1635 cm$^{-1}$ (FIG. 8B) could be assigned to C=C stretching, one must consider that, in order to avoid aging of adsorbed species, the samples were not pretreated prior to DRIFTS analyses and they could have adsorbed moisture from the environment. Water molecules produce a typical deformation band around 1640 cm$^{-1}$ when adsorbed on zeolite materials. In addition, the broad band between 2900 cm$^{-1}$ and 3500 cm$^{-1}$ displayed by both fresh and 0 minutes TOS sample spectra in FIG. 8A is an indication of H-bonded OH stretching. This band may have obscured the presence of CH stretching peaks on the blank sample spectrum (i.e., sample 0 on FIG. 8A). Note that the blank sample did desorb hydrocarbons by TPO and TPD determinations, and that a spectrum (not shown) revealing hydrocarbon-related bands was obtained when this sample was submitted to higher temperatures in the DRIFTS cell.

The bands at 1470 cm$^{-1}$ and 1367 cm$^{-1}$ (FIG. 8B) displayed on the spectra of samples 60 to 380 may be assigned to CH deformation of CH$_2$ and CH$_3$ groups. Bands at 1468 cm$^{-1}$ and 1375 cm$^{-1}$ have been assigned to deformation vibrations of the CH$_2$ and CH$_3$ groups of oligomeric species adsorbed on a zeolite catalyst, and at 1490 cm$^{-1}$ to deformations of primary or secondary carbocations or to CCC stretching of allylic carbocations. Consequently, the bands at 1470 cm$^{-1}$ and 1367 cm$^{-1}$, which broadened with TOS, indicated an increase in the number of contributing species inter alia carbocations and oligomeric species with TOS.

Typically, bands around 1580 cm$^{-1}$ to 1610 cm$^{-1}$ are assigned to coke and have been reported to arise from δ(CH) modes of a complex mixture of hydrogen-deficient carbonaceous deposits (e.g., polyethenes and/or aromatics). Neither unsaturated CH stretching above 3000 cm$^{-1}$ nor coke bands (i.e., around 1580 cm$^{-1}$ to 1610 cm$^{-1}$) were found in any of the spectra taken on samples before SFR. After SFR, the presence of hydrocarbon species was detected by TPO, although CH stretching bands were hardly noticeable on the DRIFTS spectrum of the blank experiment (0R) and the 60R sample (FIG. 9A).

None of the regenerated samples presented obvious CH deformation bands at around 1470 cm$^{-1}$ and 1367 cm$^{-1}$ (not shown) as they did before SFR. This behavior leads us to propose that the bands at 1470 cm$^{-1}$ and 1367 cm$^{-1}$ correspond to relatively low molecular weight carbocations or oligomers that were desorbed and extracted from the zeolite pores by the SFR process. A band around 1540 cm$^{-1}$, ascribed to alkylnaphthalenes or polyphenylene structures, appeared on the spectra of samples submitted to the longest TOS (280R and 360R in FIG. 9B). In addition, a coke band at 1598 cm$^{-1}$ that increased with TOS is apparent on those two sample spectra. These two bands, along with the low intensity of the saturated CH stretching bands, suggest the unsaturated nature of the hydrocarbons remaining on the regenerated catalyst samples that were reactivated after reaching their last two stages of deactivation (i.e., the rapid deactivation and the last stage).

Therefore, the comparison of DRIFTS spectra of samples before and after SFR indicates that the SFR process extracted an important number of the species that covered the zeolite surface. However, samples that were regenerated after having reached their last stages of deactivation contained some hydrocarbon species that, instead of being extracted, dehydrogenated to produce more condensed hydrocarbon species. This change may be due to the longer TOSs under the alkylation reaction and the higher temperature used for regeneration when compared to the alkylation reaction temperature, which both allowed for formation of heavier coke precursors. The aging of adsorbed hydrocarbons may also be produced by repeated reaction/regeneration cycles. USY zeolite samples submitted to four consecutive 180 minutes TOS reaction/60 minutes SFR cycles at an OWHSV of 0.5 g butene/(g catalyst×h), and their TPO and spectroscopic measurements demonstrated the presence of condensed hydrocarbon species both before and after the last regeneration cycle.

The ability of a supercritical fluid to facilitate the hydride transfer reaction between the supercritical fluid and the deactivating high-molecular weight carbocations has been suggested as an important property needed to attain high levels of catalyst activity recovery. For regeneration initiated once the sample has been submitted to alkylation for long TOSs, the diminished number of acid active sites strong enough to catalyze hydride transfer reactions between isobutane and adsorbed carbocations may also play a role in the incomplete removal of high temperature desorbing hydrocarbons.

UV-V is diffuse reflectance absorption spectra of samples before SFR (FIG. 10) revealed at least monoenylic (315 nm) and dienylic (383 nm) carbocations on samples submitted to reaction for up to 280 minutes TOS. Alkylcarbocations show no ultraviolet absorption above 210 nm. It is evident that the fast deactivation stage, in which the sample 280 was recovered, implies the onset of polycyclic aromatic compound formation. The last deactivation stage involves a lack of mono-unsaturated carbocations and the presence of neutral unsaturated species that can be noticed by the occurrence of a UV-V is band around 425 nm.

Generally, DRIFTS and UV-Vis spectra of samples before SFR displayed features that suggest that the chemical species adsorbed are large alkanes and alkenes, along with highly unsaturated and highly branched species containing cyclic structures, which are increasingly aromatic as temperature increases. After SFR (FIG. 11), none of the samples displayed important peaks corresponding to unsaturated carbocations. However, polycyclic compounds (absorbing at 425 nm) were obvious on the 180R, 280R, and 360R sample spectra. Comparing FIGS. 10 and 11, the change in hydrocarbon nature due to the SFR process is apparent. Before SFR, unsaturated carbocations were detected on all but the most deactivated sample (380) and, after SFR, mostly polycyclic aromatic compounds were the unsaturated species remaining on the catalyst surface of the longer TOS samples (180R-360R). Presumably, the first TPO peak of samples after SFR is due to low molecular weight hydrocarbons, likely isobutane, and the second one comes from compounds that produced both the UV-Vis band around 425 nm and the 1598 cm$^{-1}$ DRIFTS band. One may propose that although they are unsaturated species, their degree of condensation, at least on the sample submitted to 180 minutes TOS, is not extremely high. Note that although there is a 425 nm UV-Vis band (curve 180R in FIG. 11), all hydrocarbons desorbed below 673 K and no $CO_2$ was detected in the TPO of the 180R sample. On the other hand, before SFR and because of the higher concentration of adsorbed hydrocarbons, hydrocarbon restructuring from aliphatic to aromatic upon TPO heating may contribute to the $CO_2$ peak in TPO measurements.

Heavier and more aromatic compounds, such as the ones detected after regeneration of samples submitted to longer TOS, are expected to produce a more toxic effect on catalyst activity recovery, as described in the Ginosar '821 patent. In the Ginosar '821 patent, the effect of regeneration was determined at different catalyst deactivation levels on catalyst activity recovery. In the Ginosar '821 patent, recycle plug flow experiments utilizing multiple reaction/regeneration runs at OWHSV of 0.2 g butene/(g catalyst×h) were performed, which is a lower OWHSV than that utilized herein. When the first reaction experiment was conducted until the catalyst activity dropped to 95% (i.e., 6.5 hours TOS under the conditions at which their experiments were performed) and the rest of reaction steps were maintained for 6.5 hours each, only about 45% of catalyst activity recovery was found after 8 reaction/regeneration cycles. Percentage catalyst activity recovery was defined as the integrated product yield per gram of catalyst with respect to the first reaction step integrated yield. Furthermore, each reaction step showed that the catalyst deactivated faster than on the previous one, and 95% of initial activity was reached in shorter times, which was about 4 hours in the last reaction step. On the other hand, catalyst activity and product yields scarcely decreased after 23 regeneration steps, remaining at 100% of initial activity over the entire course of the experiment when the regeneration step was initiated using 3 hours of alkylation as the regeneration criterion.

In conclusion, the alkylation reaction produced a decrease in USY zeolite surface area and pore volume due to the adsorption of hydrocarbon species mainly in the supercages of the USY zeolite structure. The molecular weight of those species, mostly highly branched paraffins, increased with TOS. In addition, at longer TOS, neutral unsaturated hydrocarbons were detected by Uv-V is spectroscopy. The SFR process was effective in recovering surface area and micropore volume. The SFR process extracted most coke precursors from samples that were submitted to SFR after relatively short TOS under alkylation reaction conditions, when the levels of activity for TMP production were the highest. Samples that were initially allowed to react for longer TOS (until reaching the fast deactivation and the last stage) may have contained some hydrocarbon species, such as cyclic structures, that instead of being extracted by the supercritical fluid, dehydrogenated to produce more condensed hydrocarbon species. This change may have been due to the longer TOS, which allowed for an increase in the molecular weight and amount of coke precursors, and the higher temperature used for regeneration.

Example 2

The Effect of Pore Size on the Supercritical Fluid Regeneration

The effect of pore size on the supercritical fluid regeneration of a deactivated alkylation catalyst was determined. Two zeolites having different pore size distributions were used to catalyze the alkylation reaction of isobutane and 2-butene to form TMP. One of the zeolites was a USY zeolite (CBV 500) and the second zeolite was a Beta zeolite (CP 814N). The USY zeolite has a FAU framework structure, a $SiO_2/Al_2O_3$ ratio of 5.2, and cages or cavities in its pore structure. The Beta zeolite has a BEA framework structure and a $SiO_2/Al_2O_3$ ratio of 18, but does not have cages or cavities in its pore structure.

Figure 12:
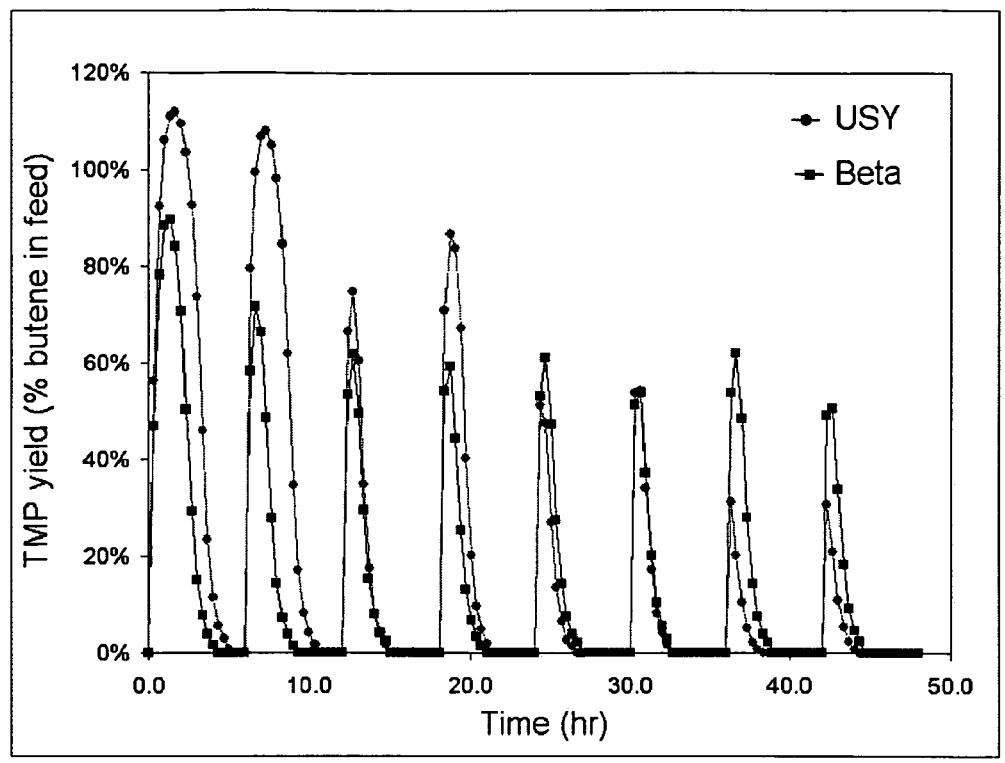
FIG. 12 shows a plot of trimethylpentane yield as a function of time.
Figure 13:
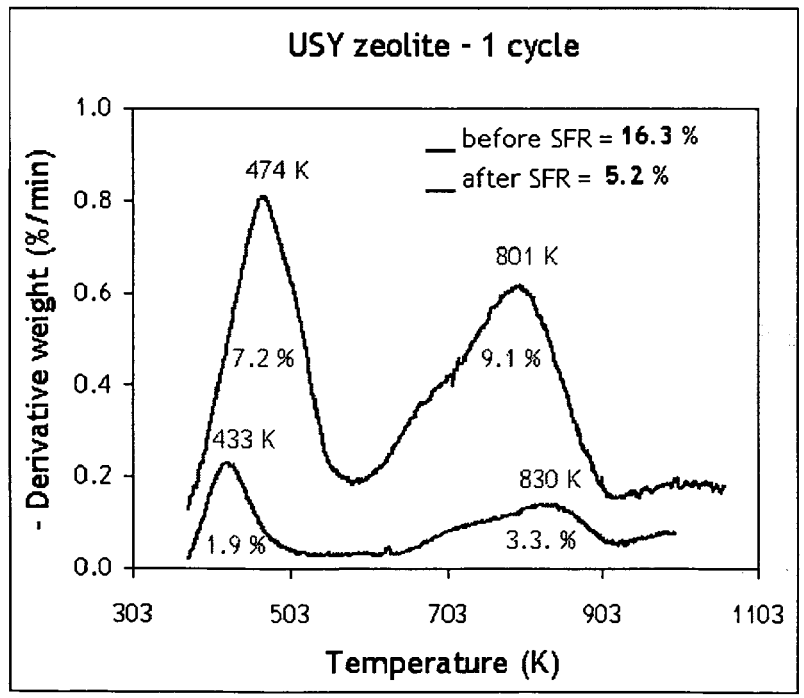
FIGS. 13 and 14 show TPO plots of USY zeolite.
Figure 14:
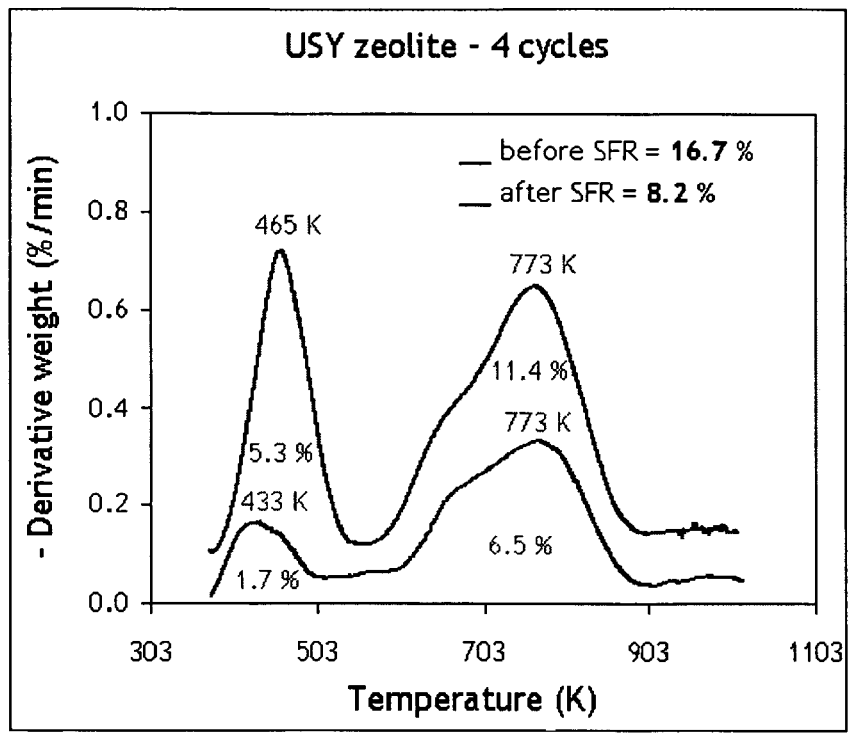
Figure 15:
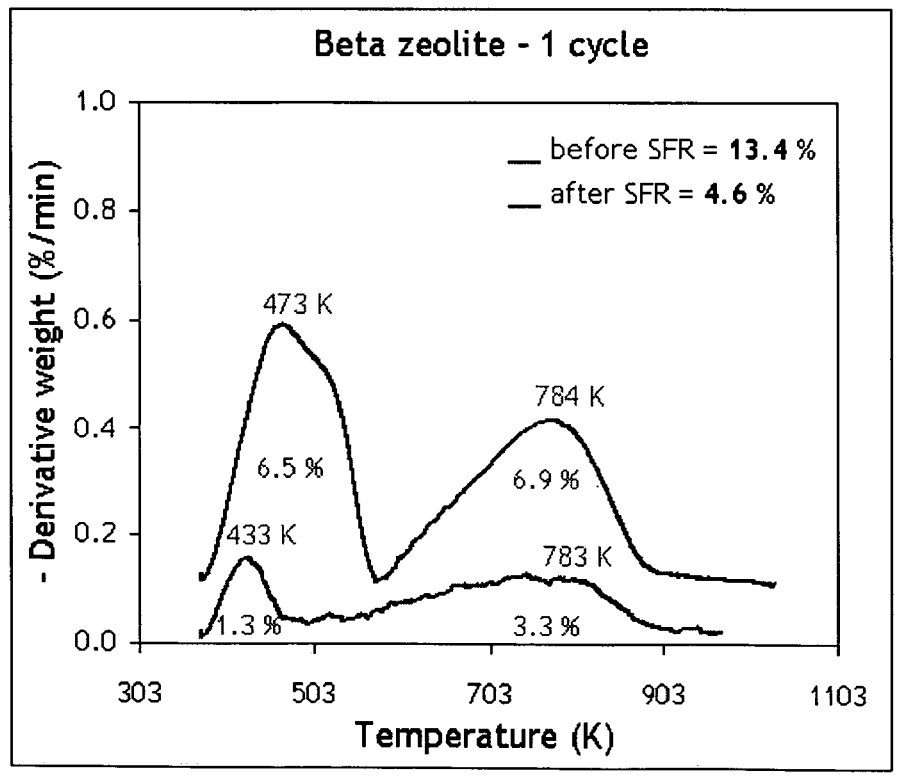
FIGS. 15 and 16 show TPO plot of Beta zeolite.
Figure 16:
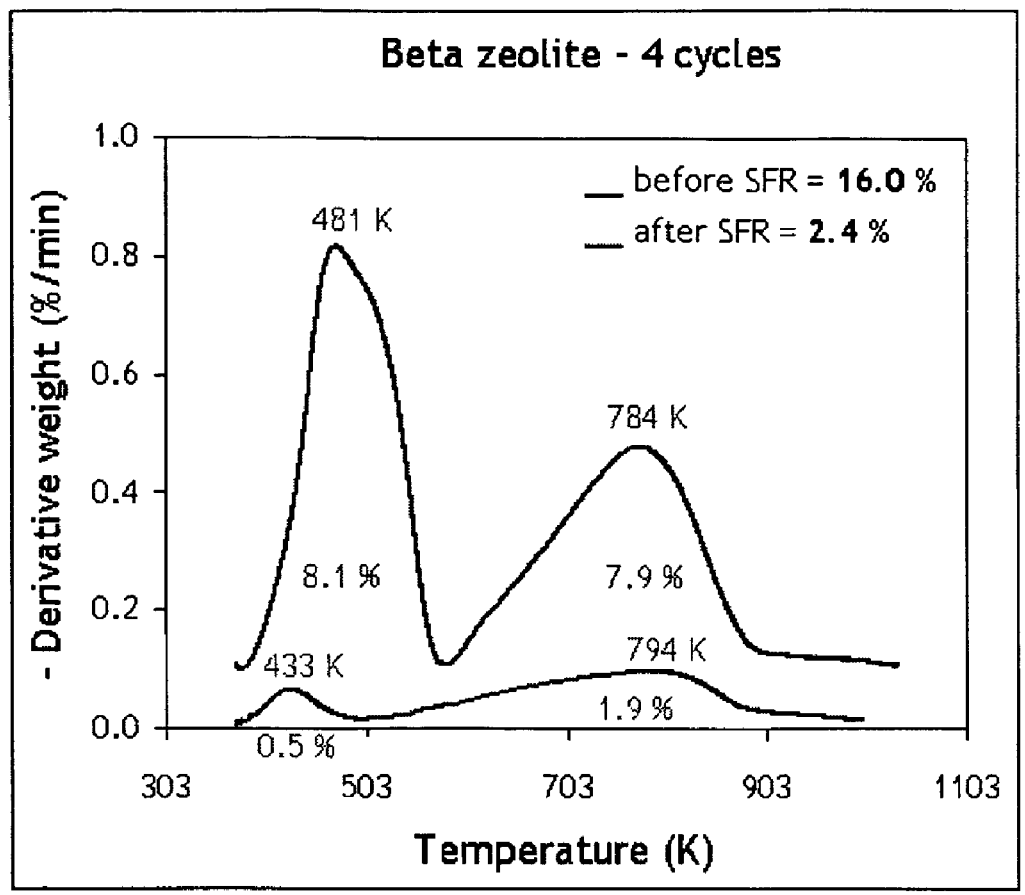
Figure 17:
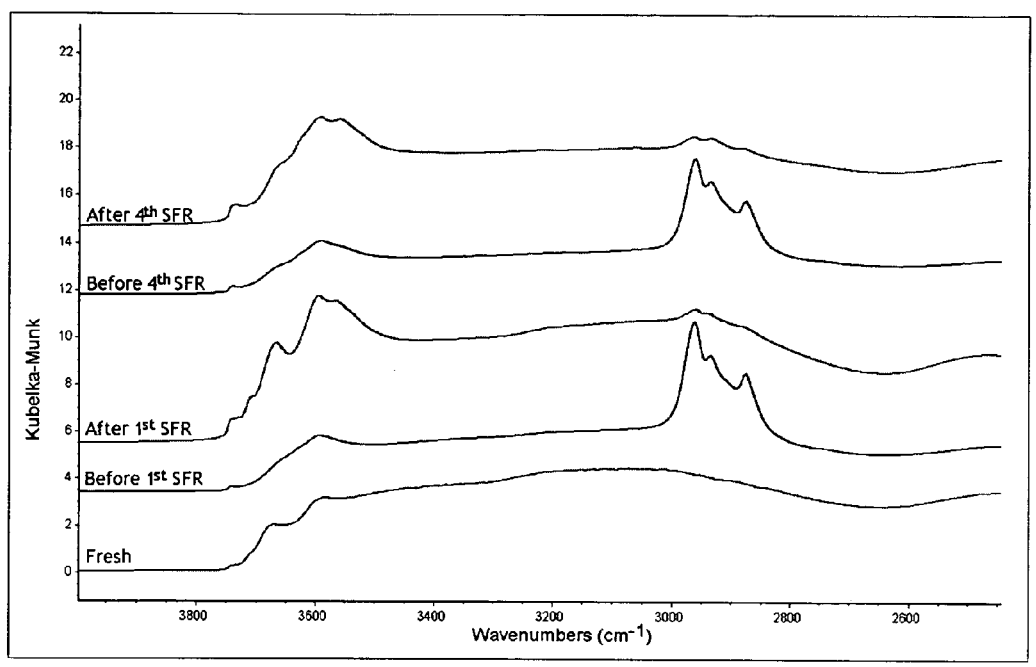
FIG. 17 shows DRIFTS spectra in the CH and OH stretching region of USY zeolite samples before and after SFR.
Figure 18:
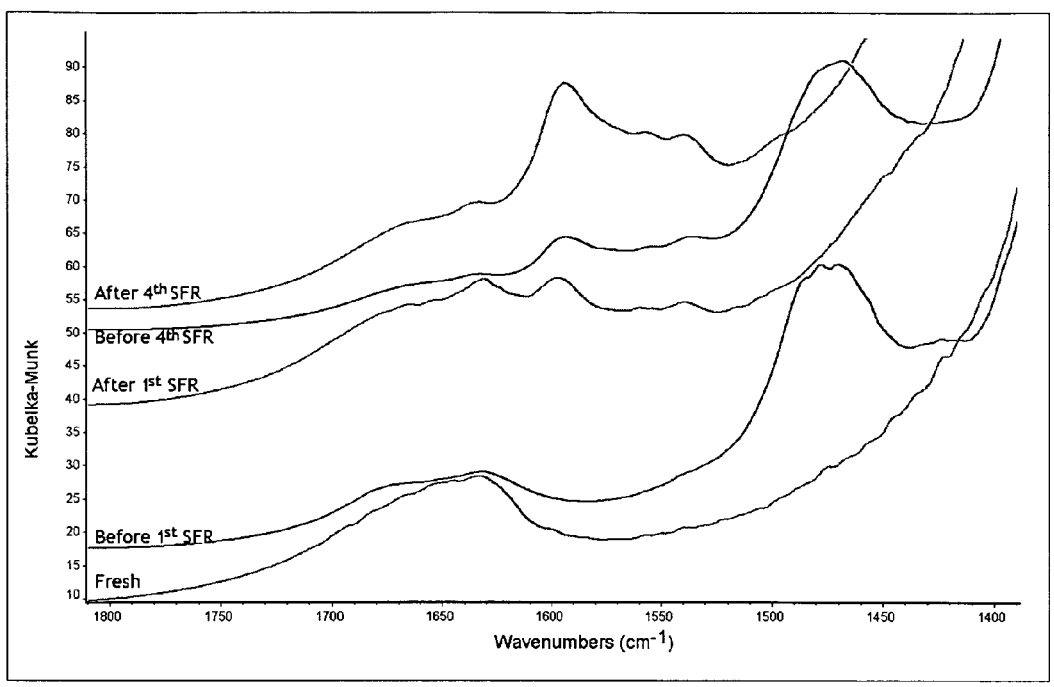
FIG. 18 shows DRIFTS spectra in the CC stretching and CH deformation region of USY zeolite samples before and after SFR.
Figure 19:
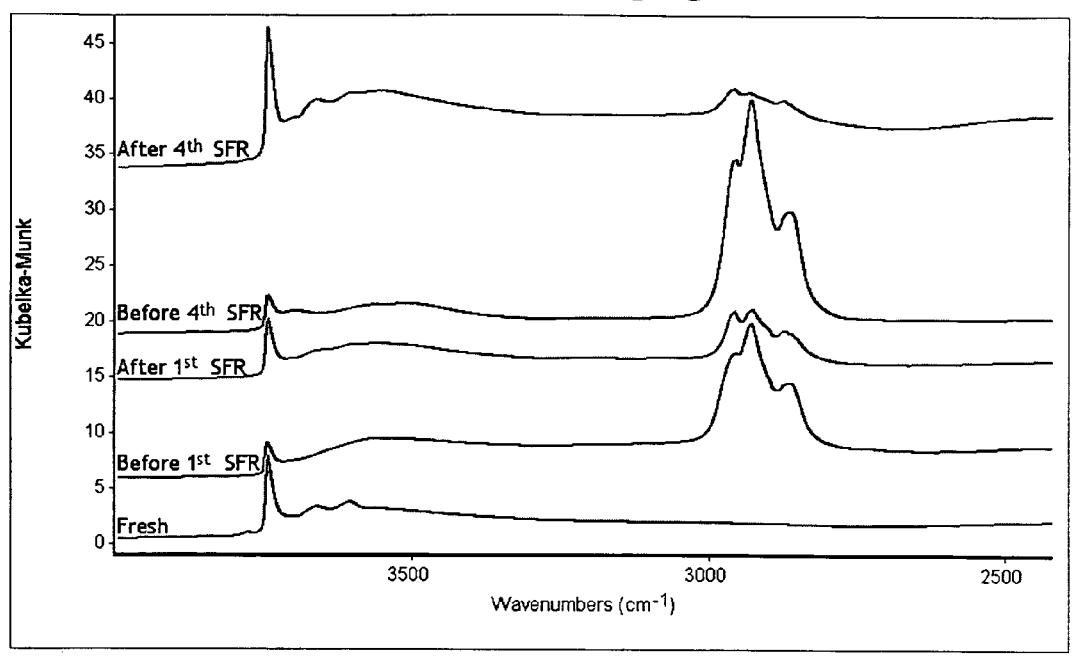
FIG. 19 shows DRIFTS spectra in the CH and OH stretching region of Beta zeolite samples before and after SFR.
Figure 20:
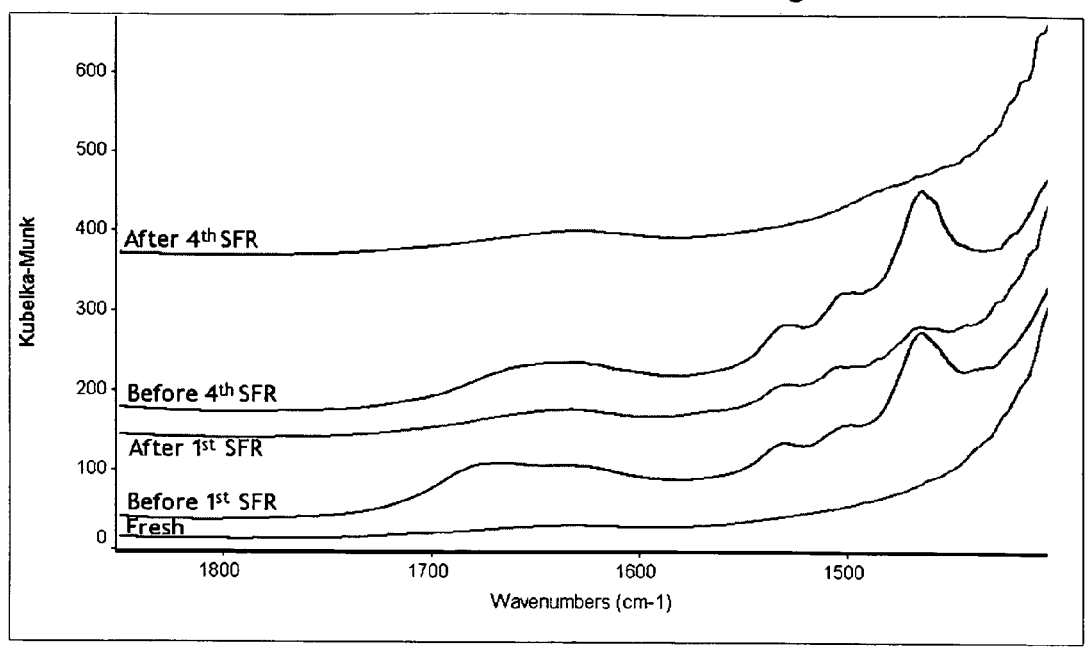
FIG. 20 shows DRIFTS spectra in the CC stretching and CH deformation region of USY zeolite samples before and after SFR.
Figure 21:
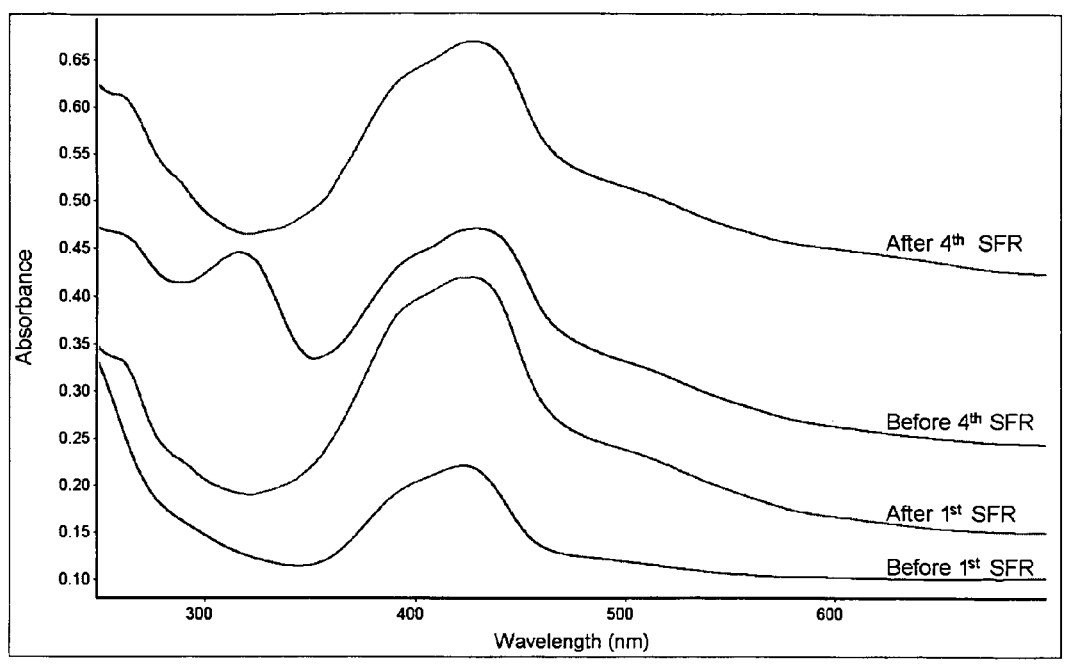
FIG. 21 shows UV-Vis spectra of USY zeolite samples before and after SFR.
Figure 22:
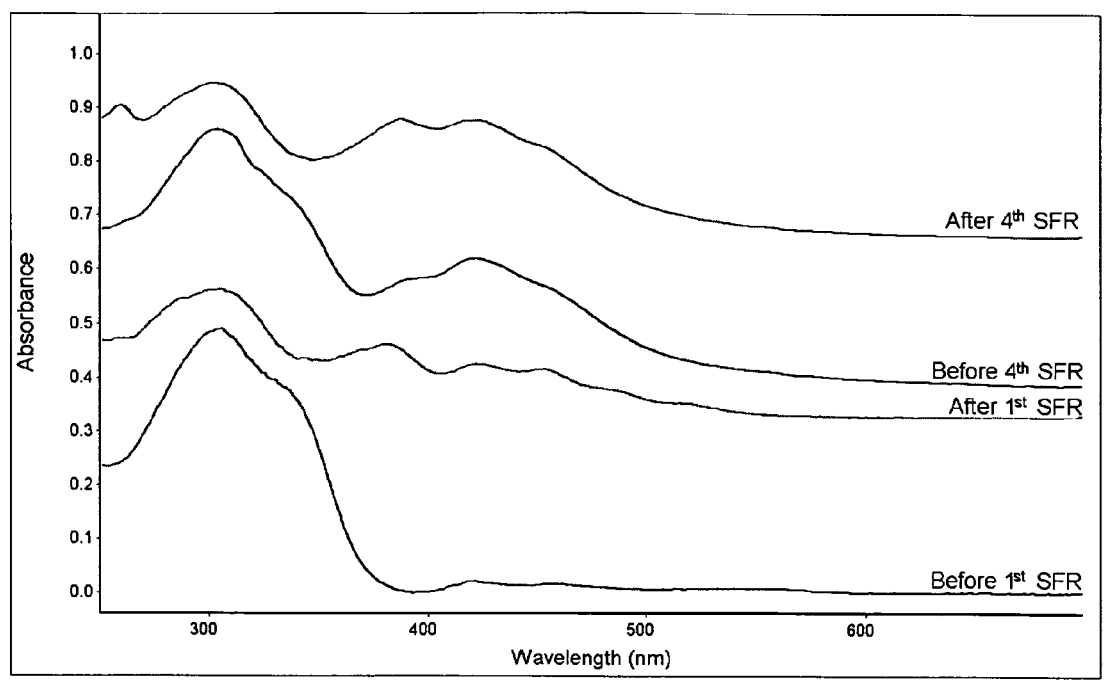
FIG. 22 shows UV-Vis spectra of Beta zeolite samples before and after SFR.

The alkylation reaction was conducted in a reactor operated in partial recycle mode for the alkylation reaction and single pass mode for the supercritical fluid regeneration. A single reactor was operated for one-cycle experiments. Two reactors were operated in swing mode for four-cycle experiments. A premixed 20:1 molar ratio of isobutane:2-butene was used as the feedstock at an OWVSV of 0.5 hours. The alkylation reaction was performed for six hours at 60° C. and 111 bar. The supercritical fluid regeneration was performed at 180° C. for 60 minutes under 2 ml/minute of isobutane. As shown in FIG. 12, the USY zeolite initially had higher yields of TMP than the Beta zeolite. However, after repeated reaction/regeneration cycles, the Beta zeolite displayed higher stability.

TPO, DRIFTS, and UV-Vis spectroscopy measurements were performed on each of the zeolites before and after the supercritical fluid regeneration. The TPO, DRIFTS, and UV-V is spectroscopy measurements were conducted as previously described. The results of these analyses are shown in FIGS. 13-22.

The surface area ("SA") and the micropore volume ("MPV") of each of the zeolites were determined by conventional techniques before and after the supercritical fluid regeneration ("SFR"), as shown in Table 5.

TABLE 5

Surface Area and Micropore Volume of the USY-zeolite and the Beta-zeolite.

| | | | USY zeolite | Beta zeolite |
|---|---|---|---|---|
| | Fresh | SA (m²/g) | 768 | 628 |
| | | MPV (cm³/g) | 0.28 | 0.19 |
| Spent one-cycle | Before 1$^{st}$ SFR | SA (m²/g) | 107 | 204 |
| | | MPV (cm³/g) | 0.00 | 0.00 |
| | After 1$^{st}$ SFR | SA (m²/g) | 645 | 477 |
| | | MPV (cm³/g) | 0.24 | 0.10 |
| Spent four-cycle | Before 4$^{th}$ SFR | SA (m²/g) | 89 | 156 |
| | | MPV (cm³/g) | 0.00 | 0.00 |
| | After 4$^{th}$ SFR | SA (m²/g) | 465 | 602 |
| | | MPV (cm³/g) | 0.16 | 0.15 |

The results show that the supercritical fluid regeneration was more effective in recovering surface area and micropore volume in the Beta zeolite than in the USY zeolite. Without being bound to a particular theory, it is believed that fewer condensed hydrocarbon species were able to form on the Beta zeolite due to the lack of cages or cavities.

Example 3

The Effect of Zeolite Acidity and Pore Structure on the Nature of Coke Precursors and SFR The effect of zeolite acidity and pore structure on the nature of coke precursors and the effectiveness of SFR was determined. A series of 12 member-ring zeolites ("12 MR") was submitted to an isobutane/butene alkylation reaction at 333 K and $1.1 \times 10^7$ Pa and supercritical isobutane regeneration at 453 K and $1.1 \times 10^7$ Pa. The zeolite samples were fully deactivated by running the liquid phase alkylation reaction for 6 hours and regenerated under flowing supercritical isobutane for 60 minutes. Zeolite samples were recovered and analyzed before and after SFR. A continuous flow reaction/regeneration experimental system was employed in the alkylation reaction. The reactants included a premixed 20:1 molar ratio of isobutane/2-butene feed for the reaction step. The OWHSV was 0.5 $h^{-1}$. Isobutane was utilized both to pressurize the system before reaction and to regenerate the zeolites. Samples of the product stream during the reaction were analyzed by gas chromatography every 20 minutes. Zeolite samples were recovered before and after SFR and submitted to $N_2$ physisorption, TPO, DRIFTS, and UV-Vis spectroscopy measurements, the results of which are summarized in Table 6. The acidity of fresh samples was determined by ammonia chemisorption.

TABLE 6

Results for Acidity, Octane Yield, Hydrocarbon Content, and Zeolite Surface Area.

| Sample* (Si/Al ratio) | Acidity (µmol/g) | Octane yield (%) | Hydrocarbons by TPO | | % SA w.r.t fresh sample | |
|---|---|---|---|---|---|---|
| | | | Spent | Regenerated | Spent | Regenerated |
| CBV 712$^y$ (6) | 509 | 15 | 3.9 | 0.0 | 63 | 87 |
| CBV 720$^y$ (15) | 213 | 7 | 1.4 | 0.1 | 87 | 98 |
| CP 814 N$^b$ (9) | 741 | 42 | 11.5 | 2.6 | 32 | 76 |
| CP 814 E$^b$ (12.5) | 345 | 19 | 10.0 | 8.4 | 28 | 36 |
| KL$^l$ (3) | 944 | 1 | 3.1 | 2.4 | 13 | 12 |
| CBV 21 A$^m$ (10) | 642 | 3 | 5.9 | 3.2 | 8 | 21 |

*Superscripts stand for: Y (y), beta (b), L (l), and mordenite (m) zeolites.

During alkylation and for similar ranges of acidity, the beta zeolites produced higher octane yields and higher amounts of coke precursors than the Y-zeolites. The loss of surface area due to the alkylation reaction on the L and mordenite zeolites along with the relatively low amount of adsorbed hydrocarbons indicated the easier plugging of the pores in the zeolites having one-dimensional 12 MR structures. Among all of the studied zeolites, the lowest recovery of surface area by SFR was found in the L-zeolite, likely due to significant diffusion limitations. On the other hand, the best recoveries of surface area were obtained in zeolites that presented three-dimensional pore structures, where diffusion limitations were less important. DRIFTS bands around 1590 $cm^{-1}$, which are usually assigned to hard coke species, were found only in regenerated Y-zeolite samples. This indicated that the presence of zeolite cages and a three-dimensional pore structure along with the higher temperatures utilized for the SFR (453 K) with respect to alkylation (333 K) favored hydrocarbon cyclization and condensation reactions in the Y-zeolite channels. Despite the almost complete recovery of surface area in the Y-zeolite samples, the appearance of hard coke deposits after SFR is expected to decrease the long-term recovery of activity of this zeolite after repeated reaction/regeneration cycles. Although UV-Vis studies showed the presence of unsaturated carbocations in all samples both before and after SFR, polycyclic/aromatic compounds (i.e., band around 430 nm) prevailed mainly in the Y- and L-zeolite samples.

As shown by these results, zeolite acidity and pore structure played an important role in zeolite behavior during the SFR process. Absence of cages and three-dimensional pore structures in the zeolites favored the effectiveness of the combined alkylation/SFR cycle. Among the zeolites analyzed, the beta zeolite with the higher acidity displayed the best performance by combining good octane yield during alkylation with high recovery in surface area and little formation of hard coke deposits by SFR.

While the invention may be susceptible to various modifications and alternative forms, specific embodiments have been described in detail herein by way of example only. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of improving a regeneration efficiency of an alkylation catalyst, comprising:
   providing an alkylation catalyst comprising a plurality of active sites;
   adsorbing a base to the plurality of active sites;
   exposing the alkylation catalyst to a temperature ranging from approximately 175° C. to less than approximately 200° C. to desorb the base from weakly acidic sites without desorbing the base from strongly acidic sites;
   catalyzing an alkylation reaction with the alkylation catalyst having the base adsorbed to the strongly acidic sites; and
   exposing the alkylation catalyst to supercritical fluid regeneration to substantially regenerate the alkylation catalyst.

2. The method of claim 1, wherein providing an alkylation catalyst comprising a plurality of active sites comprises providing the alkylation catalyst comprising a plurality of weakly acidic active sites, intermediate acidity active sites, and strongly acidic active sites.

3. The method of claim 1, wherein adsorbing a base to the plurality of active sites comprises exposing the alkylation catalyst to a base selected from the group consisting of ammonia, an amine, phosphine, pyridine, a substituted pyridine, acetonitrile, benzene, a benzene derivative, and mixtures thereof.

4. The method of claim 3, wherein exposing the alkylation catalyst to the base comprises exposing the alkylation catalyst to the base at a temperature ranging from approximately 100° C. to approximately 500° C.

5. The method of claim 3, wherein exposing the alkylation catalyst to the base comprises adsorbing the base to a plurality of weakly acidic active sites, intermediate acidity active sites, and strongly acidic active sites.

6. The method of claim 1, wherein exposing the alkylation catalyst to a temperature ranging from approximately 175° C. to less than approximately 200° C. to desorb the base from weakly acidic sites without desorbing the base from strongly acidic sites comprises heating the alkylation catalyst to a temperature of approximately 175° C.

7. The method of claim 1, wherein adsorbing a base to the plurality of active sites comprises selectively poisoning the strongly acidic active sites.

8. The method of claim 1, wherein catalyzing an alkylation reaction with the alkylation catalyst comprises forming hydrocarbon species on the alkylation catalyst.

9. The method of claim 1, wherein exposing the alkylation catalyst to supercritical fluid regeneration to substantially regenerate the alkylation catalyst comprises substantially removing the hydrocarbon species from the alkylation catalyst.

10. A method of improving a regeneration efficiency of an alkylation catalyst, comprising:

exposing an alkylation catalyst comprising a plurality of active sites to a base at a temperature sufficient to absorb the base to the plurality of active sites;

desorbing the base only from weakly acidic active sites of the plurality of active sites while the base remains absorbed to strongly acidic active sites of the plurality of active sites by exposing the alkylation catalyst to a temperature of at least approximately 175° C.;

catalyzing an alkylation reaction with the alkylation catalyst; and exposing the alkylation catalyst to supercritical fluid regeneration to substantially regenerate the alkylation catalyst.

11. The method of claim 10, wherein exposing an alkylation catalyst comprising a plurality of active sites to a base comprises exposing a zeolite comprising a silicon/aluminum ratio ranging from approximately 2.5 to approximately 15 to a base.

12. The method of claim 10, wherein catalyzing an alkylation reaction with the alkylation catalyst comprises forming hydrocarbon species on the alkylation catalyst.

13. The method of claim 10, wherein exposing the alkylation catalyst to supercritical fluid regeneration to substantially regenerate the alkylation catalyst comprises substantially removing the hydrocarbon species from the alkylation catalyst.

* * * * *

UNITED STATES PATENT AND TRADEMARK OFFICE
CERTIFICATE OF CORRECTION

PATENT NO. : 7,592,282 B2
APPLICATION NO. : 10/986742
DATED : September 22, 2009
INVENTOR(S) : Ginosar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 940 days.

Signed and Sealed this

Fourteenth Day of December, 2010

David J. Kappos
*Director of the United States Patent and Trademark Office*